United States Patent
Haga et al.

(10) Patent No.: US 11,880,135 B2
(45) Date of Patent: Jan. 23, 2024

(54) PHOTORESIST COMPOSITIONS AND PATTERN FORMATION METHODS

(71) Applicant: Rohm and Haas Electronic Materials LLC, Marlborough, MA (US)

(72) Inventors: Mitsuru Haga, Niigata (JP); Kunio Kainuma, Niigata (JP); Shugaku Kushida, Niigata (JP)

(73) Assignee: ROHM AND HAAS ELECTRONIC MATERIALS LLC, Marlborough, MA (US)

( * ) Notice: Subject to any disclaimer, the term of this patent is extended or adjusted under 35 U.S.C. 154(b) by 11 days.

(21) Appl. No.: 17/071,219

(22) Filed: Oct. 15, 2020

(65) Prior Publication Data

US 2021/0181629 A1 Jun. 17, 2021

Related U.S. Application Data

(60) Provisional application No. 62/915,222, filed on Oct. 15, 2019.

(51) Int. Cl.
G03F 7/004 (2006.01)
G03F 7/027 (2006.01)
(Continued)

(52) U.S. Cl.
CPC ......... *G03F 7/0045* (2013.01); *C07D 221/00* (2013.01); *C07D 221/14* (2013.01);
(Continued)

(58) Field of Classification Search
CPC ... C07D 211/94; C07D 221/00; C07D 221/14
See application file for complete search history.

(56) References Cited

U.S. PATENT DOCUMENTS 5,004,770 A * 4/1991 Cortolano ............ C08K 5/3435
524/99
5,124,378 A * 6/1992 Behrens ............... C08K 5/3435
546/186
(Continued)

FOREIGN PATENT DOCUMENTS

CN 102221782 A 10/2011
CN 103488048 A * 1/2014 ............. G03F 7/004
(Continued)

OTHER PUBLICATIONS

Machine translation of JP 2016-089085 (no date).*
(Continued)

*Primary Examiner* — Amanda C. Walke
(74) *Attorney, Agent, or Firm* — CANTOR COLBURN LLP

(57) ABSTRACT

Disclosed herein is a method comprising forming a radiation-sensitive film on a substrate; wherein the radiation-sensitive film comprises a radiation-sensitive composition comprising a photoacid generator; a quencher; an acid labile polymer formed from monomers comprising a vinyl aromatic monomer and a monomer comprising an acid decomposable group; and a solvent; patternwise exposing the radiation-sensitive film to activating radiation; and contacting the radiation-sensitive film with an alkaline developing solution to form a resist pattern.

9 Claims, 7 Drawing Sheets

(51) Int. Cl.
*G03F 7/085* (2006.01)
*G03F 7/32* (2006.01)
*C07D 221/00* (2006.01)
*C07D 221/14* (2006.01)
*C08F 212/14* (2006.01)
*C07D 211/94* (2006.01)
*C08F 220/18* (2006.01)

(52) U.S. Cl.
CPC .............. *G03F 7/027* (2013.01); *G03F 7/085* (2013.01); *G03F 7/322* (2013.01); *C07D 211/94* (2013.01); *C08F 212/24* (2020.02); *C08F 220/18* (2013.01)

(56) References Cited

U.S. PATENT DOCUMENTS

| | | | | |
|---|---|---|---|---|
| 5,258,138 | A * | 11/1993 | Gatechair | C07C 51/50 544/38 |
| 7,879,525 | B2 | 2/2011 | Washio et al. | |
| 8,445,178 | B2 * | 5/2013 | Park | G03F 7/031 430/326 |
| 8,980,525 | B2 * | 3/2015 | Yasuda | G03F 7/0397 430/315 |
| 9,558,833 | B2 | 1/2017 | Maejima | |
| 2012/0184101 | A1 * | 7/2012 | Yasuda | G03F 7/0397 430/326 |
| 2016/0291467 | A1 * | 10/2016 | Sugihara | G03F 7/0751 |
| 2018/0188648 | A1 | 7/2018 | Haga et al. | |

FOREIGN PATENT DOCUMENTS

| | | | | |
|---|---|---|---|---|
| CN | 106030417 | A | | 10/2016 |
| JP | H1152575 | A | | 2/1999 |
| JP | 2001249451 | A | | 9/2001 |
| JP | 2004004669 | A | | 1/2004 |
| JP | 2004198944 | A | | 7/2004 |
| JP | 4318944 | B2 | | 8/2009 |
| JP | 4318945 | B2 | | 8/2009 |
| JP | 2013145281 | A * | 7/2013 | .......... C08F 290/147 |
| JP | 2016089085 | A | | 5/2016 |
| TW | 200619838 | A | | 6/2006 |
| TW | 201107372 | A | | 3/2011 |
| TW | 201142515 | A | | 12/2011 |
| TW | 201439127 | A | | 10/2014 |
| WO | WO-2011037036 | A1 * | 3/2011 | .......... G03F 7/0045 |
| WO | WO-2016080375 | A1 * | 5/2016 | ............. G03F 7/004 |
| WO | WO-2018029142 | A1 * | 2/2018 | .......... G03F 7/0045 |
| WO | 2018047688 | A1 | | 3/2018 |
| WO | WO-2018069274 | A1 * | 4/2018 | ............ C08F 212/08 |

OTHER PUBLICATIONS

Al-Malaika et al.; "Additives for Plastics"; Brydson's Plastics Materials, Elsevier, 2017, pp. 127-168.

Aritome et al.; "A novel three-dimensional dual control-gate with surrounding floating-gate (DC-SF) NAND flash cell"; Solid-State Electronics; 79; Jan. 2013; p. 166-171.

Franssila et al.; "Chapter Twenty Two MEMS Lithography"; Handbook of Silicon Based MEMS Materials and Technologies: Elsevier, 2010, pp. 333-348.

Huang et al.; Intermetallic Formation of Copper Pillar With Sn—Ag—Cu for Flip-Chip-On-Module Packaging: IEEE Transactions on Components and Packaging Technologies; vol. 31, No. 4; Dec. 2008, pp. 767-775.

Jeong et al.; "A 128 GB 3b/cell V-NAND Flash Memory With 1 GB/s I/O Rate"; IEEE Journal of Solid-State Circuits, vol. 51, No. 1; Jan. 2016, pp. 204-212.

Korczynski,"3D-NAND Deposition and Etch Integration";file:///C:/Users/SProulx/AppData/Local/Microsoft/Windows/ INetCache/Content.Outlook/R8D1H8BM/Ref-7_3D-NAND%20deposition%20and%20etch%20integration%20_%20Semiconductor%20Digest.html;Accessed Jan. 15, 2021.

Luo et al.; "Method to Improve the Process Efficiency for Copper Pillar Electroplating"; Journal of the Electrochemical Society; 163 (3); Jan. 2016, pp. E39-E42.

Malval et al.; "Photochemistry of Naphthalimide Photoacid Generators"; J. Phys. Chem. A; 112, Feb. 2008; pp. 3879-3885.

Szycher; "Oxygen Inhibition"; Szycher's Handbook of Polyurethanes (2nd Edition), Taylor & Francis, 2013, pp. 511-512.

Ver-Bruggen; "3D NAND: To 10nm and beyond"; C:\Users\SProulx\AppData\Local\Microsoft\Windows\INetCache\Content.Outlook\R8D1H8BM\Ref-6_3D NAND_ To 10nm and beyond_ Semiconductor Digest (002).mhtml; Accessed Jan. 15, 2021.

* cited by examiner

FIG. 6

| PEB Condition | PED | #7 Troger's Base Benzotrizole Lutonal M40 | #8 Troger's Base Benzotrizole Pionine M400 | #9 Tinuvin-123 Lutonal M40 | #10 Tinuvin-123 Pionin M400 |
|---|---|---|---|---|---|
| 90°C / 60sec | 0h | | | | |
| | 24h | | | | |
| 100°C / 60sec | 0h | | | | |
| | 24h | | | | |
| 110°C / 60sec | 0h | | | | |
| | 24h | | | | |

| Sample | TEMPO analogue | Weight loss at 135°C on TG | Cross section SEM 25μm 1:1 CH pattern | |
|---|---|---|---|---|
| | | | X 15,000 At entrance o CH | X 1000 |
| #1 | 4H-TEMPO | 3.7wt% | 50mJ/cm² | |
| #2 | 4H-TEMP | 25.7wt%% | 50mJ/cm² | |
| #3 | 4-Benzoate-TEMPO | None | 50mJ/cm² | |
| #4 | 4-Acetamide-TEMPO | 0.4wt% | 60mJ/cm² | |
| #5 | 4-Methoxy-TEMPO | 46.4wt% | 50mJ/cm² | |
| #6 | TINUVIN-123 | None | 60mJ/cm² | |

FIG. 7

PHOTORESIST COMPOSITIONS AND PATTERN FORMATION METHODS

CROSS REFERENCE TO RELATED APPLICATIONS

This is a Non-Provisional application which claims the benefit of U.S. Provisional Application No. 62/915,222, filed Oct. 15, 2019, which is incorporated by reference in its entirety herein.

BACKGROUND

Disclosed herein are photoresist compositions and methods of manufacture thereof. The photoresist compositions are used for pattern formation and for packaging of chips.

Mobile devices such as wearable electronics are increasingly becoming smaller, lighter and thinner than similar devices manufactured a few years ago. Micro-processors and memory chips used in these devices are continuously shrinking in size while increasing in performance capabilities. The manufacture and packaging of these electronic devices serves an important role in the size reduction. For example, flip-chip packaging methods have been used to increase the density of I/O (Input/Output) connections between devices, especially for micro-processing unit (MPU) and dynamic random-access memory (DRAM) semiconductor chips.

Metal pillar bumps such as, for example, copper pillar bumps are often used as a flip chip interconnect for use in electronics and optoelectronic packaging, including: flip chip packaging of CPU and GPU integrated circuits (chips), laser diodes, and semiconductor optical amplifiers (SOA). Metal pillar bumps provide beneficial connection resistance, high-density connections, metal migration resistance, and thermal dissipation properties.

Electroplating has often been used for the fabrication of copper pillar bump arrays. A dry film resist (DFR) is attached to a thin sputtered copper film surface and a mask pattern having a contact-hole array is then manufactured using photolithography. Pillars are then formed in the contact-hole pattern on the copper surface by electroplating. The photoresist is then removed and the thin sputtered copper layer that was previously covered by the resist is removed by etching. I-line (365 nm) or broad band lithography has been used to image plating mask patterns.

Another approach to the preparation of plating mask patterns is the use of thick photoresist layers to respond to the need for thicker and narrower pillar sizes for further increases in I/O density. Chemically amplified photoresists may be a suitable option for achieving the faster sensitivity and improved transparency desired for higher resolution patterns. Such resist compositions include a polymer having acid labile groups, a photoacid generator (PAG), and a solvent. However, when chemically amplified resists are formed on a metal layer, such as a copper layer, footing profile issues have been observed due to photoacid present at the interface between the metal surface and the resist.

Resist compositions comprising benzotriazole (BTA), benzimidazole and triazole to prevent footing issue are known (see JP2004198944A, WO2006059392A and JP2001249451A). However, there remains a need for new methods and resist compositions which can provide a micro mask pattern on a metallic layer.

SUMMARY

Disclosed herein is a radiation-sensitive composition comprising a photoacid generator; a quencher that has the structure of formula (1)

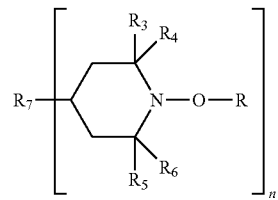

wherein $R_3$ to $R_6$ can be the same or different and are substituted or unsubstituted alkyls having 2 to 10 carbon atoms and wherein R is a radical or a substituted or unsubstituted alkyl having 1 to 10 carbon atoms, wherein $R_7$ is a group having the structure of formula (2):

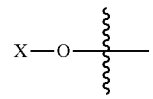

where X is a carbonyl group, an ester group, a carbonate group, an amine group, an amide group, a urea group, a sulfate group, a sulfone group, a sulfoxide group, an N-oxide group, a sulfonate group, a sulfonamide group, or a combination thereof, a substituted or unsubstituted $C_6$ to $C_{14}$ aryl group, or $C_3$ to $C_{12}$ heteroaryl group, wherein the substitution is halogen, hydroxyl, cyano, nitro, $C_1$ to $C_{12}$ alkyl group, $C_1$ to $C_{12}$ haloalkyl group, $C_1$ to $C_{12}$ alkoxy group, $C_3$ to $C_{12}$ cycloalkyl group, amino, $C_2$-$C_6$ alkanoyl, carboxamido, a substituted or unsubstituted $C_6$ to $C_{14}$ aryl group, or $C_3$ to $C_{12}$ heteroaryl group; wherein n is 1 or 2; an acid labile polymer formed from monomers comprising a vinyl aromatic monomer and a monomer comprising an acid decomposable group; and a solvent.

Disclosed herein too is a method comprising forming a radiation-sensitive composition comprising a photoacid generator; a quencher that has the structure of formula (1)

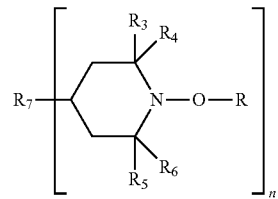

wherein $R_3$ to $R_6$ can be the same or different and are substituted or unsubstituted alkyls having 2 to 10 carbon atoms and wherein R is a radical or a substituted or unsubstituted alkyl having 1 to 10 carbon atoms, wherein $R_7$ is a group having the structure of formula (2):

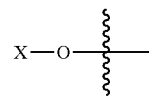

where X is a carbonyl group, an ester group, a carbonate group, an amine group, an amide group, a urea group, a sulfate group, a sulfone group, a sulfoxide group, an N-oxide group, a sulfonate group, a sulfonamide group, or a combination thereof, a substituted or unsubstituted $C_6$ to $C_{14}$ aryl group, or $C_3$ to $C_{12}$ heteroaryl group, wherein the substitution is halogen, hydroxyl, cyano, nitro, $C_1$ to $C_{12}$ alkyl group, $C_1$ to $C_{12}$ haloalkyl group, $C_1$ to $C_{12}$ alkoxy group, $C_3$ to $C_{12}$ cycloalkyl group, amino, $C_2$-$C_6$ alkanoyl, carboxamido, a substituted or unsubstituted $C_6$ to $C_{14}$ aryl group, or $C_3$ to $C_{12}$ heteroaryl group; wherein n is 1 or 2; an acid labile polymer formed from monomers comprising a vinyl aromatic monomer and a monomer comprising an acid decomposable group; and a solvent; patternwise exposing the radiation-sensitive film to activating radiation; and contacting the radiation-sensitive film with an alkaline developing solution to form a resist pattern.

BRIEF DESCRIPTION OF THE FIGURES

FIG. 6 shows that a combination of a polymeric plasticizer and a hindered amine (that has a Norrish-type cleavage structure) produced favorable pattern profiles before and after PED; and FIG. 7 shows a comparison of HALS analogues on a pattern profile of 25 μm (micrometers) for a 1:1 contact hole.

DETAILED DESCRIPTION

Figure 1:
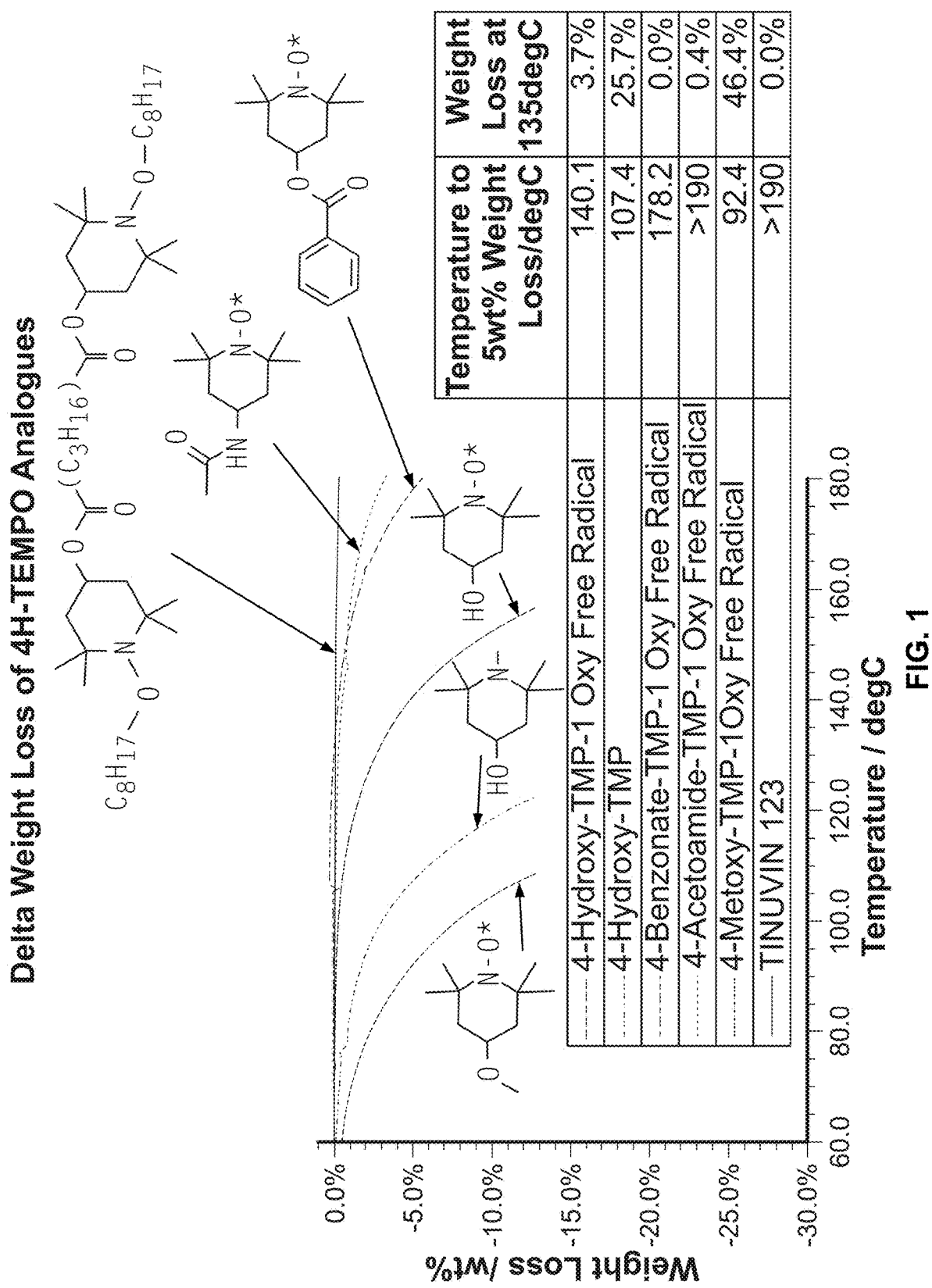
FIG. 1 depicts the results for the thermogravimetric analysis/differential thermal analysis of the various quenchers.

In this disclosure, "actinic rays" or "radiation" means, for example, a bright line spectrum of a mercury lamp, far ultraviolet rays represented by an excimer laser, extreme ultraviolet rays (EUV light), X-rays, particle rays such as electron beams and ion beams, or the like. In addition, in the present invention, "light" means actinic rays or radiation.

Furthermore, "exposure" in the present specification includes, unless otherwise specified, not only exposure by a mercury lamp, far ultraviolet rays represented by an excimer laser, X-rays, extreme ultraviolet rays (EUV light), or the like, but also writing by particle rays such as electron beams and ion beams.

In the present specification, "(a value) to (a value)" means a range including the numerical values described before and after "to" as a lower limit value and an upper limit value, respectively.

A dash ("-") that is not between two letters or symbols is used to indicate a point of attachment for a substituent. For example, —(CH$_2$)C$_3$-C$_8$ cycloalkyl is attached through carbon of the methylene (CH$_2$) group.

In the present specification, "(meth)acrylate" represents "at least one of acrylate and methacrylate." In addition, "(meth)acrylic acid" means "at least one of acrylic acid and methacrylic acid".

"Alkanoyl" is an alkyl group as defined herein, covalently bound to the group it substitutes by a keto (—(C=O)—) bridge. Alkanoyl groups have the indicated number of carbon atoms, with the carbon of the keto group being included in the numbered carbon atoms. For example a $C_2$ alkanoyl group is an acetyl group having the formula CH$_3$(C=O)—.

The term "alkyl", as used herein, means a branched or straight chain saturated aliphatic hydrocarbon group having the specified number of carbon atoms, generally from 1 to about 12 carbon atoms. The term $C_1$-$C_6$ alkyl as used herein indicates an alkyl group having from 1, 2, 3, 4, 5, or 6 carbon atoms. Other embodiments include alkyl groups having from 1 to 8 carbon atoms, 1 to 4 carbon atoms or 1 or 2 carbon atoms, e.g. $C_1$-$C_6$ alkyl, $C_1$-$C_4$ alkyl, and $C_1$-$C_2$ alkyl. When $C_0$-$C_n$ alkyl is used herein in conjunction with another group, for example, (cycloalkyl)$C_0$-$C_4$ alkyl, the indicated group, in this case cycloalkyl, is either directly bound by a single covalent bond ($C_0$), or attached by an alkyl chain having the specified number of carbon atoms, in this case 1, 2, 3, or 4 carbon atoms. Examples of alkyl include, but are not limited to, methyl, ethyl, n-propyl, isopropyl, n-butyl, 3-methylbutyl, t-butyl, n-pentyl, and sec-pentyl.

The term "cycloalkyl", as used herein, indicates a saturated hydrocarbon ring group, having only carbon ring atoms and having the specified number of carbon atoms, usually from 3 to about 8 ring carbon atoms, or from 3 to about 7 carbon atoms. Examples of cycloalkyl groups include cyclopropyl, cyclobutyl, cyclopentyl, or cyclohexyl as well as bridged or caged saturated ring groups such as norborane or adamantane.

The term "heterocycloalkyl", as used herein, indicates a saturated cyclic group containing from 1 to about 3 heteroatoms chosen from N, O, and S, with remaining ring atoms being carbon. Heterocycloalkyl groups have from 3 to about 8 ring atoms, and more typically have from 5 to 7 ring atoms. Examples of heterocycloalkyl groups include morpholinyl, piperazinyl, piperidinyl, and pyrrolidinyl groups. A nitrogen in a heterocycloalkyl group may optionally be quaternized.

In citations for a group and an atomic group in the present specification, in a case where the group is denoted without specifying whether it is substituted or unsubstituted, the group includes both a group and an atomic group not having a substituent, and a group and an atomic group having a substituent. For example, an "alkyl group" which is not denoted about whether it is substituted or unsubstituted includes not only an alkyl group not having a substituent (unsubstituted alkyl group), but also an alkyl group having a substituent (substituted alkyl group).

The term "alkenyl", as used herein, means straight and branched hydrocarbon chains comprising one or more unsaturated carbon-carbon bonds, which may occur in any stable point along the chain. Alkenyl groups described herein typically have from 2 to about 12 carbon atoms. Exemplary alkenyl groups are lower alkenyl groups, those alkenyl groups having from 2 to about 8 carbon atoms, e.g. $C_2$-$C_8$, $C_2$-$C_6$, and $C_2$-$C_4$ alkenyl groups. Examples of alkenyl groups include ethenyl, propenyl, and butenyl groups.

The term "alkynyl", means straight and branched hydrocarbon chains comprising one or more CC carbon-carbon triple bonds, which may occur in any stable point along the chain. Alkynyl groups described herein typically have from 2 to about 12 carbon atoms. Exemplary alkynyl groups are lower alkynyl groups, those alkenyl groups having from 2 to about 8 carbon atoms, e.g. $C_2$-$C_8$, $C_2$-$C_6$, and $C_2$-$C_4$ alkynyl groups. Examples of alkynyl groups include ethynyl, propynyl, and butynyl groups.

The term "cycloalkenyl", as used herein, means a saturated hydrocarbon ring group, comprising one or more unsaturated carbon-carbon bonds, which may occur in any stable point of the ring, and having the specified number of carbon atoms. Monocyclic cycloalkenyl groups typically have from 3 to about 8 carbon ring atoms or from 3 to 7 (3, 4, 5, 6, or 7) carbon ring atoms. Cycloalkenyl substituents may be pendant from a substituted nitrogen or carbon atom, or a substituted carbon atom that may have two substituents may have a cycloalkenyl group, which is attached as a spiro group. Examples of cycloalkenyl groups include cyclopropenyl, cyclobutenyl, cyclopentenyl, or cyclohexenyl as well as bridged or caged saturated ring groups such as norbornene.

The terms "(cycloalkyl)$C_0$-$C_n$ alkyl", as used herein, means a substituent in which the cycloalkyl and alkyl are as defined herein, and the point of attachment of the (cycloalkyl)alkyl group to the molecule it substitutes is either a single covalent bond, ($C_0$alkyl) or on the alkyl group. (Cycloalkyl)alkyl encompasses, but is not limited to, cyclopropylmethyl, cyclobutylmethyl, and cyclohexylmethyl.

The terms "(heterocycloalkyl)$C_0$-$C_n$ alkyl", as used herein, means a substituent in which the heterocycloalkyl and alkyl are as defined herein, and the point of attachment of the (heterocycloalkyl)alkyl group to the molecule it substitutes is either a single covalent bond, ($C_0$ alkyl) or on the alkyl group. (Heterocycloalkyl)alkyl encompasses, but is not limited to, morpholinylmethyl, piperazinylmethyl, piperidinylmethyl, and pyrrolidinylmethyl groups.

The term "aryl", as used herein, means aromatic groups containing only carbon in the aromatic ring or rings. Typical aryl groups contain 1 to 3 separate, fused, or pendant rings and from 6 to about 18 ring atoms, without heteroatoms as ring members. When indicated, such aryl groups may be further substituted with carbon or non-carbon atoms or groups. Bicyclic aryl groups may be further substituted with carbon or non-carbon atoms or groups. Bicyclic aryl groups may contain two fused aromatic rings (naphthyl) or an aromatic ring fused to a 5- to 7-membered non-aromatic cyclic group that optionally contains 1 or 2 heteroatoms independently chosen from N, O, and S, for example, a 3,4-methylenedioxy-phenyl group. Aryl groups include, for example, phenyl, naphthyl, including 1-naphthyl and 2-naphthyl, and bi-phenyl.

The term "mono- or bicyclic heteroaryl", as used herein, indicates a stable 5- to 7-membered monocyclic or 7- to 10-membered bicyclic heterocyclic ring which contains at least 1 aromatic ring that contains from 1 to 4, or specifically from 1 to 3, heteroatoms chosen from N, O, and S, with remaining ring atoms being carbon. When the total number of S and O atoms in the heteroaryl group exceeds 1, theses heteroatoms are not adjacent to one another. Specifically, the total number of S and O atoms in the heteroaryl group is not more than 2, more specifically the total number of S and O atoms in the heteroaryl group is not more than 1. A nitrogen atom in a heteroaryl group may optionally be quaternized. When indicated, such heteroaryl groups may be further substituted with carbon or non-carbon atoms or groups. Such substitution may include fusion to a 5 to 7-membered saturated cyclic group that optionally contains 1 or 2 heteroatoms independently chosen from N, O, and S, to form, for example, a [1,3]dioxolo[4,5-c]pyridyl group. In certain embodiments 5- to 6-membered heteroaryl groups are used. Examples of heteroaryl groups include, but are not limited to, pyridyl, indolyl, pyrimidinyl, pyridizinyl, pyrazinyl, imidazolyl, oxazolyl, furanyl, thiophenyl, thiazolyl, triazolyl, tetrazolyl, isoxazolyl, quinolinyl, pyrrolyl, pyrazolyl, benz[b]thiophenyl, isoquinolinyl, quinazolinyl, quinoxalinyl, thienyl, isoindolyl, and 5,6,7,8-tetrahydroisoquinoline.

"Haloalkyl" includes both branched and straight-chain alkyl groups having the specified number of carbon atoms, substituted with 1 or more halogen atoms, up to the maximum allowable number of halogen atoms. Examples of haloalkyl include, but are not limited to, trifluoromethyl, difluoromethyl, 2-fluoroethyl, and penta-fluoroethyl.

"Haloalkoxy" is a haloalkyl group as defined herein attached through an oxygen bridge (oxygen of an alcohol radical).

"Halo" or "halogen" is any of fluoro, chloro, bromo, and iodo.

"Mono- and/or di-alkylamino" is a secondary or tertiary alkyl amino group, wherein the alkyl groups are independently chosen alkyl groups, as defined herein, having the indicated number of carbon atoms. The point of attachment of the alkylamino group is on the nitrogen. Examples of mono- and di-alkylamino groups include ethylamino, dimethylamino, and methyl-propyl-amino. Amino means —$NH_2$.

The term "substituted", as used herein, means that any one or more hydrogens on the designated atom or group is replaced with a selection from the indicated group, provided that the designated atom's normal valence is not exceeded. When the substituent is oxo (i.e., =O) then 2 hydrogens on the atom are replaced. When an oxo group substitutes aromatic moieties, the corresponding partially unsaturated ring replaces the aromatic ring. For example, a pyridyl group substituted by oxo is a pyridone. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent.

Unless otherwise specified substituents are named into the core structure. For example, it is to be understood that when (cycloalkyl)alkyl is listed as a possible substituent the point of attachment of this substituent to the core structure is in the alkyl portion, or when arylalkyl is listed as a possible substituent the point attachment to the core structure is the alkyl portion.

Suitable groups that may be present on a "substituted" or "optionally substituted" position include, but are not limited to, halogen; cyano; hydroxyl; nitro; azido; alkanoyl (such as a $C_2$-$C_6$ alkanoyl group such as acyl or the like); carboxamido; alkyl groups (including cycloalkyl groups) having 1 to about 8 carbon atoms, or 1 to about 6 carbon atoms; alkenyl and alkynyl groups including groups having one or more unsaturated linkages and from 2 to about 8, or 2 to about 6 carbon atoms; alkoxy groups having one or more oxygen linkages and from 1 to about 8, or from 1 to about 6 carbon atoms; aryloxy such as phenoxy; alkylthio groups including those having one or more thioether linkages and from 1 to about 8 carbon atoms, or from 1 to about 6 carbon atoms; alkylsulfinyl groups including those having one or more sulfinyl linkages and from 1 to about 8 carbon atoms, or from 1 to about 6 carbon atoms; alkylsulfonyl groups including those having one or more sulfonyl linkages and from 1 to about 8 carbon atoms, or from 1 to about 6 carbon atoms; aminoalkyl groups including groups having one or more N atoms and from 1 to about 8, or from 1 to about 6 carbon atoms; aryl having 6 or more carbons and one or more rings, (e.g., phenyl, biphenyl, naphthyl, or the like, each ring either substituted or unsubstituted aromatic); arylalkyl having 1 to 3 separate or fused rings and from 6 to about 18 ring carbon atoms, with benzyl being an exemplary arylalkyl group; arylalkoxy having 1 to 3 separate or fused rings and from 6 to about 18 ring carbon atoms, with benzyloxy being an exemplary arylalkoxy group; or a saturated, unsaturated, or aromatic heterocyclic group having 1 to 3 separate or fused rings with 3 to about 8 members per ring and one or more N, O or S atoms, e.g. coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such heterocyclic groups may be further substituted, e.g. with hydroxy, alkyl, alkoxy, halogen and amino.

Disclosed herein is a radiation-sensitive composition comprising a quencher; a photoacid generator; an acid labile polymer; an optional adhesion promotor; an optional aromatic azole compound; and a solvent. The radiation-sensitive composition is advantageous in that it can be used to make a radiation-sensitive film. The radiation-sensitive film can be soft-baked to minimize the solvent content in the film, thereby forming a tack-free coating and improving adhesion of the film to the substrate. The radiation-sensitive film is then exposed through a mask (having a predefined pattern disposed thereon) using radiation such as ultraviolet light (having a wavelength of from 200 to 500 nanometers (nm)) or visible light. Preferably, the exposure is conducted with radiation having a wavelength of 365 nm (i-line).

In an embodiment, the quencher has the structure of formula (1)

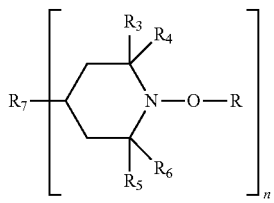

(1)

wherein $R_3$ to $R_6$ can be the same or different and are substituted or unsubstituted alkyls having 2 to 10 carbon atoms and wherein R is a radical or a substituted or unsubstituted alkyl having 1 to 10 carbon atoms, wherein $R_7$ is a hydrogen or a group having the structure of formula (2):

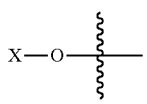

(2)

where X is a nitrogen atom, a sulfur atom, a phosphorus atom, a halogen atom, a carbonyl group, an ester group, a carbonate group, an amine group, an amide group, a urea group, a sulfate group, a sulfone group, a sulfoxide group, an N-oxide group, a sulfonate group, a sulfonamide group, a substituted or unsubstituted $C_6$ to $C_{14}$ aryl group, or $C_3$ to $C_{12}$ heteroaryl group, wherein the substitution is halogen, hydroxyl, cyano, nitro, $C_1$ to $C_{12}$ alkyl group, $C_1$ to $C_{12}$ haloalkyl group, $C_1$ to $C_{12}$ alkoxy group, $C_3$ to $C_{12}$ cycloalkyl group, amino, $C_2$-$C_6$ alkanoyl, carboxamido, a substituted or unsubstituted $C_6$ to $C_{14}$ aryl group, or $C_3$ to $C_{12}$ heteroaryl group; wherein n is 1 or 2. A suitable halogen atom is fluorine. In an embodiment, R in the structure (1) is not hydrogen. In another embodiment, $R_3$ through $R_7$ is not an amine nor an amino group.

In a preferred embodiment, the quencher of structure (2) has the structure of formula (3):

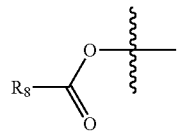

(3)

where $R_8$ is a substituted or unsubstituted aryl group having 6 to 20 carbon atoms, a fused aryl group, or a substituted or unsubstituted monovalent or divalent alkyl having 1 to 12 carbon atoms. In the structure of formula (3), n is 1 or 2.

In another preferred embodiment, the quencher may have the structures (4) through (6):

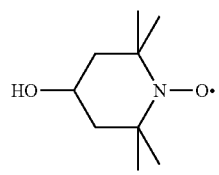

(4)

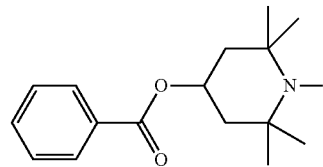

(5)

and

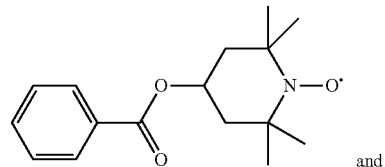

(6)

The amount of the quencher in the radiation-sensitive composition is designed based on the number of moles of the photoacid generator. For example, the quencher loading is maintained at up to 0.0001 wt % when 4H-TEMPO is selected as the quencher and the radiation-sensitive composition has a low solids content (e.g., less than 20 wt % of solids) with a low photoacid generator loading of less than 1 wt % based on the weight of the polymer. The quencher loading can be up to 1.2 wt % when TINUVIN-123 is selected with a large solids content (e.g., 50 wt % solids or greater) and a high photoacid generator (e.g., NHNI-PFBS) loading of 3 wt % or greater, based on the total weight of the radiation-sensitive composition.

In an embodiment, the mole ratio percentage of the quencher to the photoacid generator (expressed as a percentage) is 5 to 50%, preferably 8 to 30%, and most preferably 10 to 15%.

The quencher of structures (1) through (6) may be used in the radiation-sensitive composition in amounts of 0.0001 wt % to 1.2 wt %, based on a total weight of the radiation-sensitive composition. In a preferred embodiment, the quencher of structures (1) through (6) may be used in the radiation-sensitive composition in amounts of 0.001 wt % to 0.8 wt %, based on a total weight of the radiation-sensitive composition.

The radiation-sensitive composition includes a photoacid generator (PAG). It is desirable to use photoacid generators that generate the photoacid by a Norrish-1 cleavage. The Norrish-I reaction is the photochemical cleavage or homolysis of aldehydes and ketones into two free radical intermediates. The carbonyl group accepts a photon and is excited to a photochemical singlet state. In an embodiment, the photoacid generator has the structure shown in formula (7)

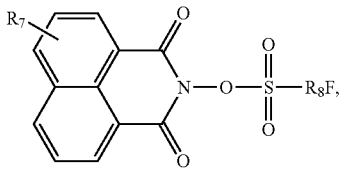

(7)

where in formula (7), $R_7$ is a hydrogen atom, a substituted or unsubstituted, linear or branched $C_1$ to $C_{14}$ alkyl group, a substituted heterocyclic group, or a halogen atom; and wherein $R_8$ is a substituted or unsubstituted alkyl group having 1 to 18 carbon atoms; a halogen atom, or an aryl group having 6 to 20 unsubstituted carbon atoms.

Examples of suitable photoacid generators are N-hydroxynaphthalimide trifluoromethanesulfonate, N-hydroxynaphthalimide perfluoro-1-butanesulfonate, N-hydroxynaphthalimide camphor-10-sulfonate, N-hydroxynaphthalimide 2-trifluoromethylphenylsulfonate, N-hydroxy-5-norbornene-2,3-dicarboximide perfluoro-1-butanesulfonate, N-(trifluoromethylsulfonyloxy)phthalimide or N-hydroxysuccinimide perfluorobutanesulfonate. In a preferred embodiment, the photoacid generator is fluoroalkenelsulfonyloxy-1,8-naphthalimide.

Photoacid generators can also include those suitable for the purpose of preparing photoresists. Such photoacid generators can include, for example, non-ionic oximes.

The photoacid generator is present in the radiation-sensitive composition in amount of 0.25 parts by weight or greater, 0.5 parts by weight or greater, and preferably 0.75 parts by weight or greater up to a maximum amount of 10 parts by weight per 100 parts by weight of the acid labile polymer.

In an embodiment, the photoacid generator may be present in the radiation sensitive composition in an amount of 0.3 wt % or greater, preferably 0.4 wt % or greater up to a maximum amount of 5 wt %, based on the total weight of the radiation-sensitive composition.

The radiation-sensitive composition also comprises a copolymer formed from a first repeat unit that contains an acid decomposable group and a second repeat unit that contains a vinyl aromatic monomer. This copolymer is also referred to as an acid labile polymer. In an embodiment, the first repeat unit having the labile acid group has a structure represented by formula (8):

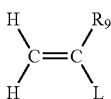

(8)

where $R_9$ is a hydrogen or an alkyl group having 1 to 10 carbon atoms and where L comprises a carbonyl group (e.g., species including aldehydes; ketones; carboxylic acids and carboxylic esters such as, for example, (meth)acrylic acids and (meth)acrylates), a single bond (e.g., a vinyl ether), or an aromatic unit (e.g., styrene or its derivatives). In an embodiment, the carboxylic ester is a tertiary alkyl ester.

In an embodiment, when L comprises a carbonyl group, the repeat unit containing the acid labile group has the structure represented by formula (9) below:

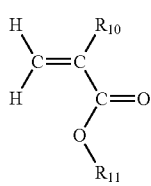

(9)

where $R_{10}$ is a hydrogen or an alkyl or haloalkyl group having 1 to 10 carbon atoms and where $R_{11}$ is a linear or branched, substituted or unsubstituted alkyl group having 1 to 10 carbon atoms, a substituted or unsubstituted, monocyclic or polycyclic cycloalkyl group having 3 to 14 carbon atoms or a tertiary alkyl ester. The cycloalkyl groups may contain one or more heteroatoms such as oxygen, sulfur, nitrogen, or phosphorus. Combinations or heteroatoms may also be used. For example, the cycloalkyl group may contain an oxygen and a nitrogen heteroatom. Repeat units having the structure of formula (9) which do not have acid labile groups may also be used in the resist polymer, so long as the resist polymer has at least one repeat unit that has an acid labile group.

Examples of other monomers that contain an acid labile group (e.g., a carbonyl group) are shown below in formula (10):

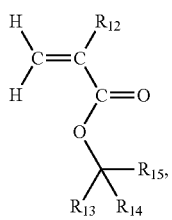

(10)

where $R_{12}$ is a hydrogen or an alkyl or haloalkyl group having 1 to 10 carbon atoms, and where $R_{13}$, $R_{14}$ and $R_{15}$ may be the same or different and are selected from a linear or branched, substituted or unsubstituted alkyl group having 1 to 10 carbon atoms, a substituted or unsubstituted, monocyclic or polycyclic cycloalkyl group having 3 to 14 carbon atoms, an aryl or a heteroaryl. The cycloalkyl groups may contain one or more heteroatoms such as oxygen, sulfur, nitrogen, or phosphorus. Combinations or heteroatoms may also be used. For example, the cycloalkyl group may contain an oxygen and a nitrogen heteroatom. In an embodiment, either $R_{13}$, $R_{14}$ or $R_{15}$ may comprise a cyclic moiety.

In an embodiment, $R_{13}$, $R_{10}$ and $R_{15}$ in the formula (10) may be the same or different and comprise hydrogen, a substituted or unsubstituted alkyl group having 2 to 8 carbon atoms that may be linear or branched or a substituted or unsubstituted cycloalkyl group having 4, 5 or 6 carbon atoms that may contain branches.

Examples of monomers that contain a carbonyl acid labile group include the following:
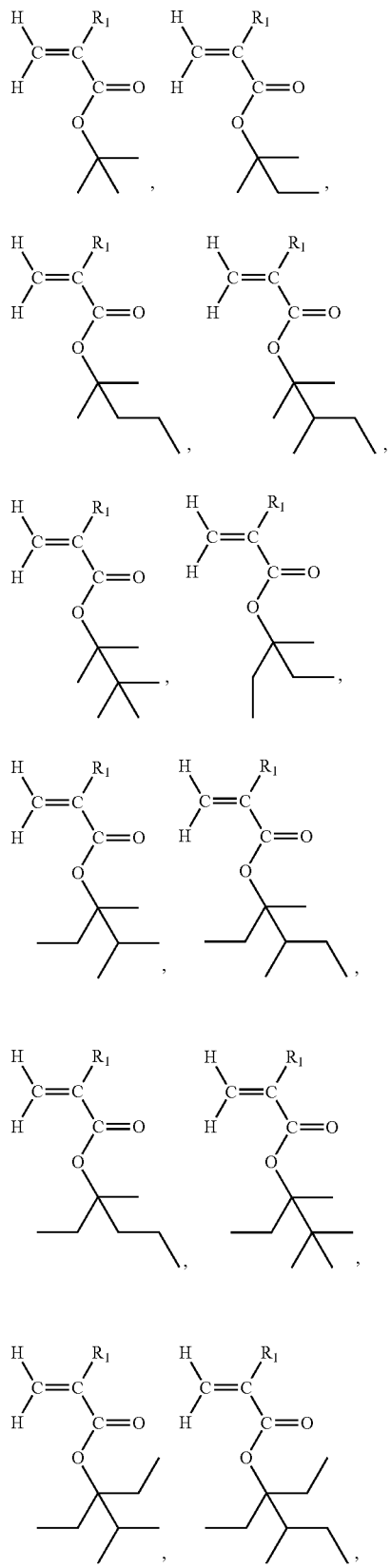
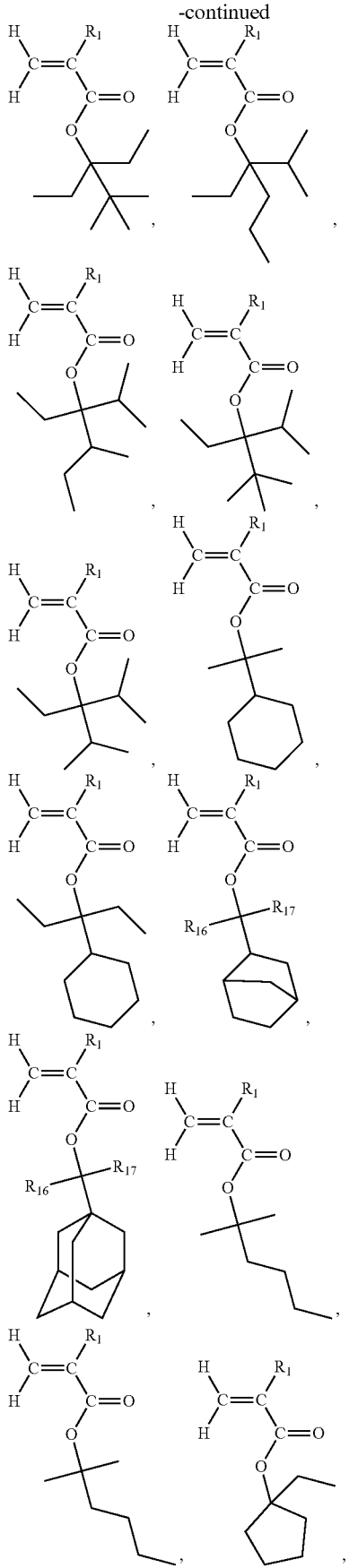

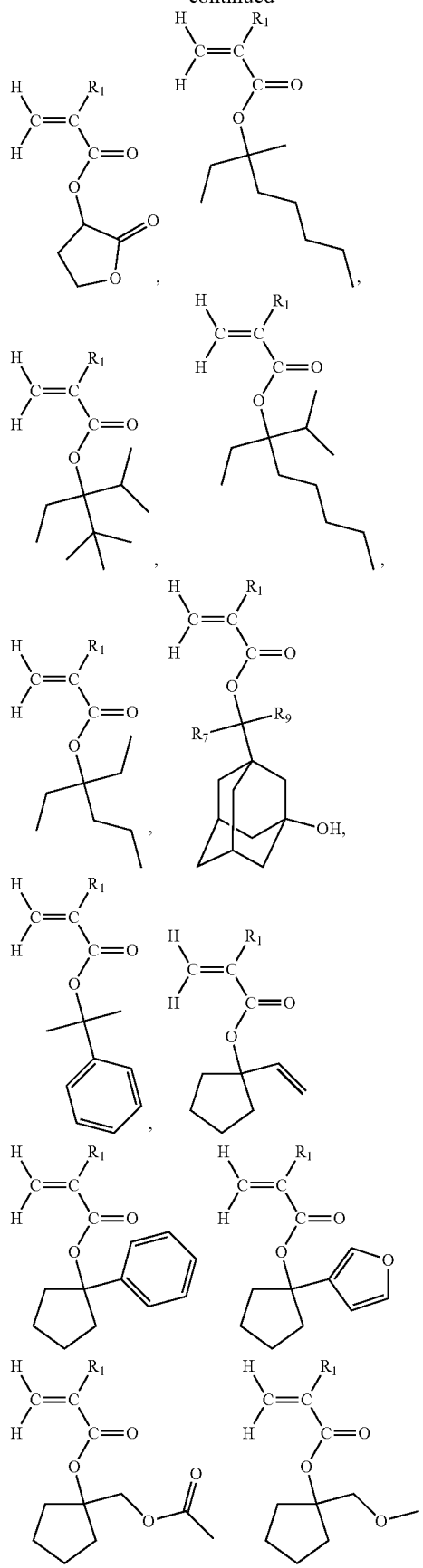

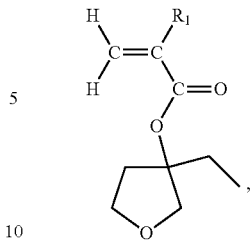

or a combination thereof; wherein where $R_1$ is a hydrogen or an alkyl or haloalkyl group having 1 to 10 carbon atoms, a halogen, or a haloalkyl group having 1 to 10 carbon atoms, and wherein $R_{16}$ is an alkyl group which may include a branched structure having 1 to 10 carbon atoms or a monocyclic or polycyclic cycloalkyl group having 3 to 14 carbon atoms; and $R_{17}$ is an alkyl group which may include a branched structure having 1 to 10 carbon atoms or a monocyclic or polycyclic cycloalkyl group having 3 to 14 carbon atoms. Preferred halogen atoms are fluorine atoms and a preferred haloalkyl group includes a fluoroalkyl group.

In an embodiment, when L in formula (8) comprises more than one carbon atom, the repeat unit containing the acid labile group has the structure represented by formula (11) below

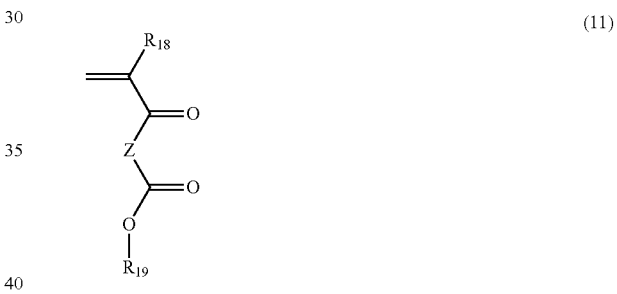

(11)

wherein Z is a linking unit comprising at least one carbon atom and at least one heteroatom, where $R_{18}$ is a hydrogen atom or an alkyl group having 1 to 10 carbon atoms; and wherein $R_{19}$ is an alkyl group which may include a branched structure having 1 to 10 carbon atoms, a monocyclic or polycyclic cycloalkyl group having 3 to 14 carbon atoms or a tertiary alkyl ester. In an embodiment, Z can have 2 to 10 carbon atoms. In another embodiment, Z can be $CH_2$—C(=O)—O—).

Specific examples of repeat units that have the structure of formula (11) are the following:

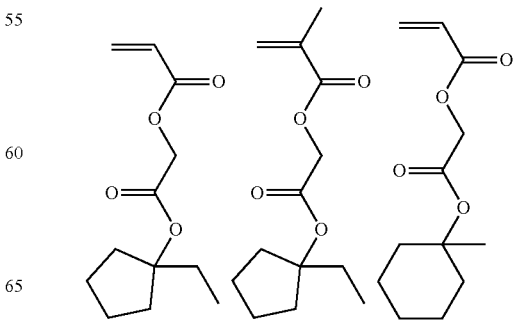

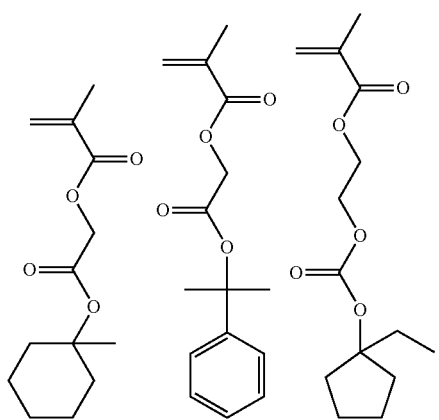
Illustrative acid-labile acetal- and ketal-substituted monomers also include:
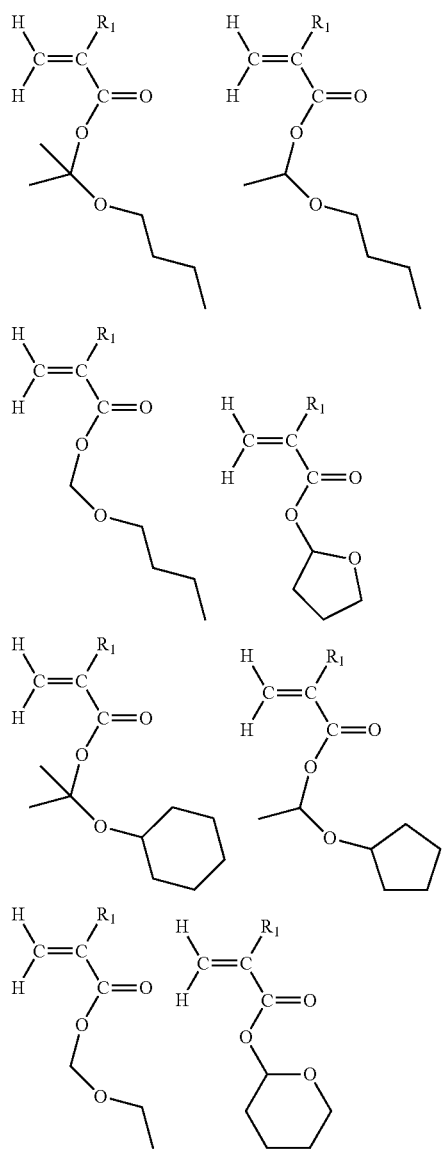
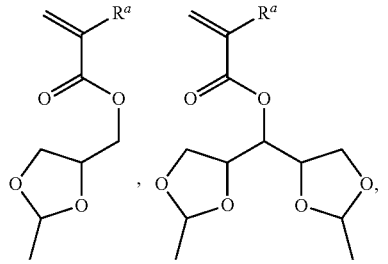
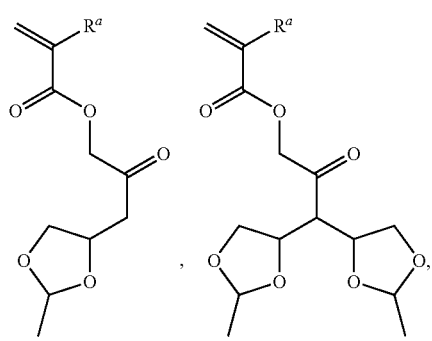
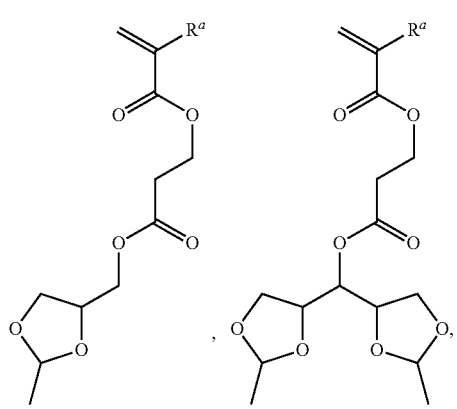
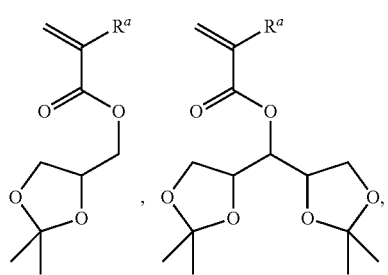
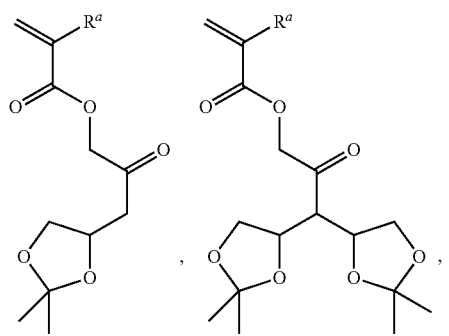

-continued

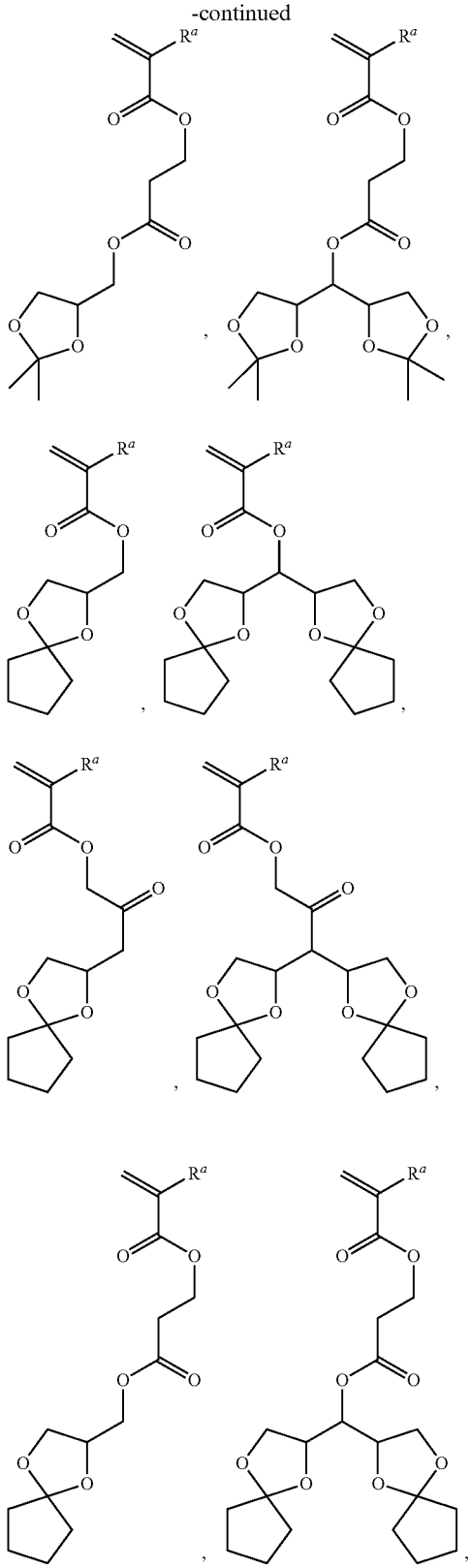

and combinations thereof, wherein $R^a$ is —H, —F, —CH₃, or —CF₃ and wherein where $R_1$ is a hydrogen or an alkyl or haloalkyl group having 1 to 10 carbon atoms, a halogen, or a haloalkyl group having 1 to 10 carbon atoms.

In another embodiment, when L (in formula (8) shown above) is an aromatic unit, the acid labile repeat unit may be a vinyl aromatic unit having the structure of formula (12):

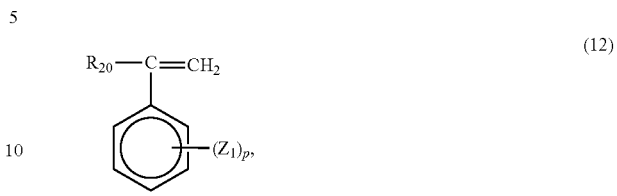

(12)

wherein $R_{20}$ is hydrogen, an alkyl or halogen; $Z_1$ is a hydroxyl or optionally a hydrogen, a halogen, an alkyl, an aryl, or a fused aryl; and p is from 1 to about 5. In an embodiment, $Z_1$ is preferably a hydroxyl.

The vinyl aromatic monomers that can be reacted to produce the resist polymer include styrenes, alkylstyrenes, hydroxystyrenes, or styrenes substituted with halogens. Examples of suitable alkylstyrenes are o-methylstyrene, p-methylstyrene, m-methylstyrene, α-methylstyrene, o-ethyl styrene, m-ethyl styrene, p-ethyl styrene, α-methyl-p-methyl styrene, 2,4-dimethylstyrene, p-tert-butylstyrene, 4-tert-butylstyrene, or the like, or a combination thereof. Examples of styrenes substituted with halogens include chlorostyrene, fluorostyrene, hydroxyfluorostyrene, or a combination thereof.

In a preferred embodiment, the acid labile repeat unit has a tertiary carbon as the acid labile group (e.g., a tertiary butyl acrylate or a tertiary butyl methacrylate). In another preferred embodiment, the vinyl aromatic monomer is 4-hydroxystyrene. Put another way, the acid labile polymer comprises a copolymer of hydroxystyrene and a (meth) acrylic monomer that comprises a tertiary carbon as an acid labile species, wherein the copolymer has a weight average molecular weight of 10,000 to 30,000 grams per mole. The molecular weight is measured using a polystyrene standard.

In yet another embodiment, the acid labile polymer may contain a third repeat unit such as a second vinyl aromatic monomer (e.g., styrene) in addition to the repeat unit that contains a first vinyl aromatic monomer (e.g., 4-hydroxystyrene) and the repeat unit that contains an acid labile group. In one preferred embodiment, the vinyl aromatic monomer comprises polyhydroxystyrene monomer. In another preferred embodiment, the vinyl aromatic monomer comprises both styrene and polyhydroxystyrene monomers.

The vinyl aromatic polymer may be present in the acid labile polymer in an amount of 40 to 90 mol %, preferably 60 to 87 mol %, based on the total number of moles of the acid labile polymer.

The acid labile repeat units may be present in an amount of 5 to 70 mol %, preferably 10 to 50 mol %, and more preferably 15 to 40 mol %, based on the total number of moles of the acid labile polymer (i.e., the copolymer). The acid labile polymer is present in the radiation-sensitive composition in an amount of 10 to 98 wt % based on a total weight of the radiation-sensitive composition. In a preferred embodiment, the acid labile polymer may be used in the radiation-sensitive composition in amounts of 30 to 55 wt %, based on a total weight of the radiation-sensitive composition.

In an embodiment, when the acid labile polymer contains repeat units of polyhydroxystyrene and tertiary butyl acrylate, the polyhydroxystyrene is present in an amount of 60 to 66 mol %, based on the total number of moles of the acid-labile polymer. In an embodiment, the tertiary butyl acrylate is present in an amount of 34 to 40 mol %, based on the total number of moles of the acid-labile polymer.

In another embodiment, when the acid labile polymer contains repeat units of polyhydroxystyrene, styrene and tertiary butyl acrylate, the polyhydroxystyrene is present in an amount of 60 to 66 mol %, preferably 62 to 65 mol %, based on the total number of moles of the acid-labile polymer. In another embodiment, the styrene is present in an amount of 15 to 22 mol %, preferably 18 to 20 mol %, based on the total number of moles of the acid-labile polymer. In another embodiment, the tertiary butyl acrylate is present in an amount of 12 to 20 mol %, preferably 13 to 17 mol %, based on the total number of moles of the acid-labile polymer.

As noted above, the radiation-sensitive composition contains a solvent. The solvent is used to solvate polymers used in the composition and to facilitate miscibility of the various ingredients used in the composition. In some embodiments, the radiation-sensitive composition in solution comprises the polymer in an amount of 40 to 90 wt %, specifically 50 to 85 wt %, more specifically 55 to 80 wt %, based on the weight of the total solids. It will be understood that "polymer" used in this context of a component in a resist may mean only the copolymer disclosed herein, or a combination of the copolymer with another polymer useful in a photoresist. It will be understood that total solids includes polymer, photo destroyable base, quencher, surfactant, any added PAG, and any optional additives, exclusive of solvent.

Solvents generally suitable for dissolving, dispensing, and coating include anisole, alcohols including 1-methoxy-2-propanol (also referred to as propylene glycol methyl ether, PGME), and 1-ethoxy-2 propanol, esters including n-butyl acetate, 1-methoxy-2-propyl acetate (also referred to as propylene glycol methyl ether acetate, PGMEA), methoxyethyl propionate, ethoxyethyl propionate, and gamma-butyrolactone, ketones including cyclohexanone, 2,6-dimethyl-4-heptanone, 2 heptanone; ethyl lactate (EL), 2-hydroxyisobutyric acid methyl ester (HBM), gamma-butyrolactone (GBL), 3-methoxypropanoic acid methyl ester, and combinations thereof.

The solvent amount can be, for example, 40 to 90 wt %, preferably 45 to 65 wt %, and more preferably 48 to 58 wt %, based on the total weight of the radiation-sensitive composition.

The radiation-sensitive composition can comprise other optional ingredients, such as one or more surface leveling agent (SLA), polymeric adhesion promoter and/or plasticizer.

If used, the SLA is preferably present in an amount of from 0.001 to 0.1 wt % based on total solids of the composition, and the adhesion promoter and/or plasticizer each in an amount of from 0.1 to 10 wt % based on total solids of the composition.

In an embodiment, the polymeric adhesion promoter is obtained by the polymerization of a monomer having the structure of formula (13)

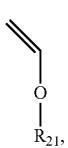

(13)

wherein $R_{21}$ is a substituted or unsubstituted alkyl group having 1 to 18 carbon atoms. In a preferred embodiment, $R_{21}$ in formula (13) is a methyl or ethyl. In an embodiment, the polymeric adhesion promotor may have a weight average molecular weight of 30,000 grams per mole or greater, preferably 50,000 grams per mole or greater, and more preferably 70,000 grams per mole or greater. The polymeric adhesion promotor may have an upper weight average molecular weight of 100,000 grams per mole or less, preferably 90,000 grams per mole or less.

The polymeric adhesion promotor may be used in an amount of 0.5 parts by weight or greater, 0.75 parts by weight or greater, and more preferably 0.85 parts by weight or greater up to a maximum amount of 20 parts by weight, based on 100 parts by weight of the acid labile polymer. In a preferred embodiment, the polymeric adhesion promotor may be used in an amount of 0.5 parts by weight or greater to 1.5 parts by weight or less, based on 100 parts by weight of the acid labile polymer.

In an embodiment, the polymeric adhesion promotor may be used in an amount of 0.25 wt % or greater, 0.4 wt % or greater up to an amount of 10 wt % or less, preferably 2 wt % or less based on the total weight of the of the radiation-sensitive composition.

In an embodiment, the radiation-sensitive composition may contain a species having a chelating functional group. In an embodiment, the radiation-sensitive composition may contain an aromatic azole compound such as a benzotriazole derivative having the structure of formula (14) shown below.

(14)

wherein $R_{22}$ is an alkyl group having 1 to 14 carbon atoms or an amine group.

The aromatic azole compound may be present in the radiation-sensitive composition in an amount of 0.01 to 10 parts by weight, preferably 0.015 to 1 part by weight, based on 100 parts by weight of the acid labile copolymer in the radiation-sensitive composition.

In an embodiment, the azole compound may be used in amounts of 0.001 to 0.5 wt %, based on a total weight of the radiation-sensitive composition. In a preferred embodiment, the azole compound may be used in amounts of 0.01 to 0.25 wt %, based on a total weight of the radiation-sensitive composition.

Processes which make use of the radiation-sensitive compositions will now be described. In accordance with a patterning process, a radiation-sensitive film is formed on a substrate from a radiation-sensitive composition as described herein. The composition can be applied to the substrate by spin-coating, dipping, roller-coating or other conventional coating technique. Spin-coating is preferred. For spin-coating, the solids content of the coating solution can be adjusted to provide a desired film thickness based upon the specific coating equipment utilized, the viscosity of the solution, the speed of the coating tool and the amount of time allowed for spinning.

The radiation-sensitive film can next be soft-baked to minimize the solvent content in the film, thereby forming a tack-free coating and improving adhesion of the film to the substrate. The soft-bake can be conducted on a hotplate or in an oven, with a hotplate being typical.

The radiation-sensitive film is then patternwise exposed to activating radiation through a photomask to create a difference in solubility between exposed and unexposed regions. References herein to exposing a radiation-sensitive film to radiation that is activating for the film indicates that the radiation is capable of forming a latent image in the film. The photomask has optically transparent and optically opaque regions corresponding to regions of the resist layer to be exposed and unexposed, respectively, by the activating radiation. The exposure wavelength is typically sub-500 nm, such as from 200 to 500 nm or visible light. Preferably, the exposure is conducted with radiation of 365 nm wavelength (i-line).

Following exposure of the radiation-sensitive film, a post exposure bake (PEB) is typically performed to decompose the acid labile group by acid that generated from the PAG during the exposure step. The PEB can be conducted, for example, on a hotplate or in an oven. A latent image defined by the boundary between polarity-switched and unswitched regions (corresponding to exposed and unexposed regions, respectively) is thereby formed.

The radiation-sensitive film is next contacted with an alkaline developing solution to remove exposed portions of the film, leaving unexposed regions forming a resist pattern. The developer is typically an aqueous alkaline developer, for example, a quaternary ammonium hydroxide solution, for example, a tetra-alkyl ammonium hydroxide solutions such as 0.26 Normality (N) (2.38 wt %) tetramethylammonium hydroxide (TMAH).

A further aspect of the invention is a process for depositing a metal on a metal layer. The process includes: (i) forming a radiation-sensitive film on a metal layer; (ii) patternwise exposing the radiation-sensitive film to activating radiation; (iii) a post exposure bake step to decompose the acid labile group; (iv) contacting the radiation-sensitive film with an alkaline developing solution to remove exposed portions of the radiation-sensitive film; and (v) immersing the metal layer in a metal plating solution and electro depositing a metal on the metal layer in the exposed portions of the radiation-sensitive film. The metal layer is typically formed on a substrate.

The metal layer can be made, for example, of copper, silver, aluminum, gold or an alloy thereof. The metal layer may also be referred to herein as the first metal layer. When the metal layer is formed on a substrate, the metal layer can be formed using known methods, for example, by chemical vapor deposition (CVD) or physical vapor deposition (PVD) techniques, with sputtering and plating being typical. The thickness of the metal layer is typically from 10 nm to 1000 nm. Examples of the substrate include, but are not limited to, silicon wafers, glass substrates and plastic substrates, such substrates optionally including one or more layers or features formed thereon.

The radiation-sensitive film is formed from the radiation-sensitive composition as described herein, comprising: a quencher; a photoacid generator; an acid labile polymer; an optional adhesion promotor; an optional aromatic azole compound; and a solvent. The radiation-sensitive composition is applied on the metal layer by a known method, such as spin-coating, roll coating or screen printing. To form a thick radiation-sensitive film, a high solids content and/or high viscosity radiation-sensitive composition is typically desired. The solid content of the composition is typically from 10 to 60 wt %, preferably from 20 to 50 wt %, based on the total weight of the radiation-sensitive composition.

By using such a composition, a thick layer, for example, of 10 micrometers or greater, preferably from 20 to 120 micrometers, can be formed.

After applying the radiation-sensitive composition, soft baking can be conducted to minimize the solvent content in the layer and to improve adhesion of the layer to the substrate. The radiation-sensitive film is then exposed through a mask having a predefined pattern using radiation such as ultraviolet light having a wavelength of from 200 to 500 nanometers (nm) or visible light. Preferably, the exposure is conducted with radiation of 365 nm wavelength (i-line).

The radiation-sensitive film is contacted with an alkaline developing solution to develop the exposed portions of the radiation-sensitive film. Examples of the alkaline developing solution include aqueous solutions of tetramethyl ammonium hydroxide, sodium hydroxide and potassium hydroxide. The exposed portions can form a pattern such as a hole (e.g., contact, via or bump pattern) or trench (e.g., line-space) pattern. Such patterns preferably have a high aspect ratio. As used herein, aspect ratio (AR) is defined as AR=h/d, wherein h is the photoresist height (i.e., thickness) and d is the spacing in the pattern, for example, hole diameter (e.g., for contact, via or bump patterns) or length of space between adjacent lines (e.g., for trench patterns). Typically, the hole diameter can be from 2 to 200 micrometers, preferably from 10 to 50 micrometers. The aspect ratio is typically 0.1 or more, 0.5 or more, from 0.1 to 10.0, or from 0.5 to 7.0.

The substrate can next be immersed in a metal plating solution to plate metal on the exposed first metal layer in those regions in which the radiation-sensitive film has been developed away. The developed regions of the radiation-sensitive film function as a mold for the metal plating. The metal can be plated, for example, by electroplating. Various types of metal plating solutions known in the art can be used. Also, two or more different layers of metal can be formed, and the layers can be of the same or different metals. Preferable plated metals include, but are not limited to, copper, nickel, tin, silver, gold and mixtures and alloys thereof. Suitable metal plating solutions for use in forming such metals are known in the art and are commercially available from Dow Electronic Materials. The thickness of the plated metal layer is typically from 1 to 100 micrometers, preferably from 20 to 50 micrometers. The plated metal layer thickness can be less than or exceed the thickness of the photoresist layer.

After metal plating, the remaining radiation-sensitive film can be removed (stripped) from the substrate. Suitable photoresist strippers are commercially available, for example, Shipley BPR™ Photostripper (Dow Electronic Materials).

The exposed first metal layer between the plated metal structures can be removed, for example, by etch-back process, to electrically isolate each of the plated metal structures. The obtained metal structures can have, for example, a pillar shape, which can be useful for a metal bump for providing electrical connection between two components. Advantageously, metal pillars having small-diameter and straight (vertical) sidewalls can be formed by compositions and methods disclosed herein. Such structures find use, for example, in electrical connections in small, light and thin devices. The width (diameter) of the pillars can, for example, be from 5 to 200 micrometers, preferably from 10 to 50 micrometers. The height of the pillars will depend, for example, on the thickness of the radiation-sensitive resin, but pillar heights of 20 micrometers or more can be formed.

The invention will now be exemplified by the following non-limiting examples.

EXAMPLE

Example 1

This example was conducted to determine the quenchers that produce the least weight loss when heated to elevated temperatures.

Quenchers such as hindered amine light stabilizers (HALS) are often used to control photo acid generation in the fluorinated naphtalimide photoacid generator. Reaction scheme I shows a proposed mechanism for acid photogeneration in perfluorinated napthalimides.

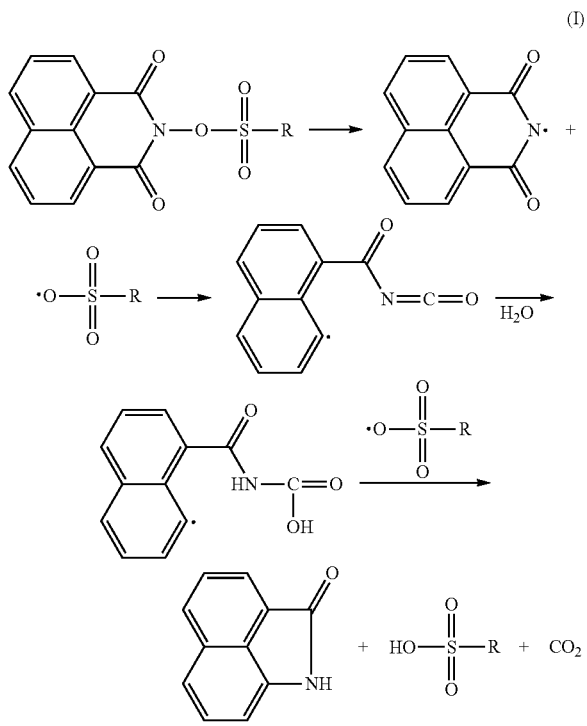

R = CF$_3$, C$_4$F$_9$

The mechanism of radical quenching of HALS produces a different effect compared with a conventional amine base quencher as seen in reaction scheme II below.

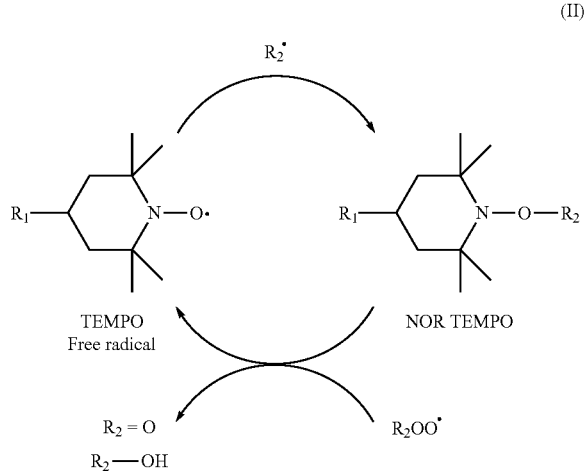

Reaction scheme II depicts a radical quenching mechanism for hindered amine light stabilizers (HALS). Hindered amine light stabilizers (HALS) are often used as antioxidants in plastics or coatings. During heating processes in plastics or in a coating fabrication process, an effective amount of the HALS needs to be retained in the matrix in order to perform its intended function. Lower molecular weight compounds generally degrade at higher temperatures which reduces physical leaching out at higher temperatures. In this application, a photoresist is applied to a coating and undergoes a soft bake cure process at 135° C. for 1 to 6 minutes. At this temperature, a portion of the HALS in the composition may evaporate or be sublimated.

Sublimation or evaporation of the hindered amine light stabilizer from photo resist or anti-reflective coatings (when heated) have produced some quality control issues in the manufacture of electronic devices because of the production of particulate matter caused by the evaporation or sublimation. The severity of this damage produced by sublimation becomes stronger due to film thickness, where thicker films (i.e., between 10 to 50 micrometers) can entrap more matter because of film thickness. In this section, thermal weight loss and decomposition or melting points were measured for selection of passivation compounds. Thermal weight loss was measured by thermogravimetric analysis/differential thermal analysis (TGA/DTA). Al$_2$O$_3$ was used as the reference. An aluminum open pan with nitrogen flow was applied. The heating rate was 5° C./min. Table 1 details the test conditions for the shows the thermogravimetric analysis/differential thermal analysis.

TABLE 1

| Tool | TGDTA6200, SII/Hitachi |
|---|---|
| Flow | N$_2$, 160 ml/min |
| Ref | Al$_2$O$_3$ |
| Method | Al pan, open |
| Ramp rate | 5° C./min |
| Sample size | 7-14 milligrams |

The quenchers that were subjected to the thermogravimetric analysis/differential thermal analysis test are 4-methoxy-TMP-1-oxy free radical, 4-hydroxy-TMP and 4-hydroxy-TMP-1-oxy free radical, 4-benzoate-TMP-1-oxy free radical, 4-acetoamide-TMP-1-oxy free radical and TINUVIN® 123. TINUVIN® 123 is a liquid hindered amine light stabilizer (HALS) based on an amino-ether functionality.

The results for the thermogravimetric analysis/differential thermal analysis is shown in the FIG. 1. 4-methoxy-TMP-1-oxy free radical, 4-hydroxy TMP and 4-hydroxy-TMP-1-oxy free radical displayed a higher than 3% weight loss at 135° C. in the TG-DTA test. TMP-1-oxy stands for tetramethyl-1-piperidinyloxy. TMP stands for tetramethyl piperidine.

Example 2

This example was conducted to determine the effect of HALS compounds to the pattern profile. The aforementioned quenchers (i.e., HALS compounds) 4-methoxy-TMP-1-oxy free radical, 4-hydroxy-TMP and 4-hydroxy-TMP-1-oxy free radical, 4-benzoate-TMP-1-oxy free radical, 4-acetoamide-TMP-1-oxy free radical and Tinuvin® 123 were used as a base quencher in an iCAR photoresist.

The nomenclature for this example is shown in the Table 1a.

TABLE 1a

| Acronym | Chemical name | Purchased from |
|---|---|---|
| 4H-TEMPO | 4-hydroxy-2,2,6,6-tetramethylpiperidine 1-oxyl free radical | Tokyo Chemical Industry Co., LTD. |
| 4H-TEMP | 4-hydroxy-1,2,2,6,6-pentamethylpiperidine | Tokyo Chemical Industry Co., LTD |
| 4-Benzoate-TEMPO | 4-hydroxy-2,2,6,6-tetramethylpiperidine 1-oxyl benzoate free radical | Tokyo Chemical Industry Co., LTD. |
| 4-Acetamide-TEMPO | 4-acetamido-2,2,6,6-tetramethylpiperidine 1-oxyl free radical | Tokyo Chemical Industry Co., LTD. |
| 4-Methoxy-TEMPO | 4-methoxy-2,2,6,6-tetramethylpiperidine 1-oxyl free radical | Tokyo Chemical Industry Co., LTD. |
| TINUVIN-123 | | BASF Japan |

Table 2 shows the formulation (compositions) for the i-line chemical amplification photoresist (iCAR) samples. HALS analogs were used as base quenchers. The amount of quencher was chosen such that the quencher/PAG molar ratio was 0.139. TINUVIN-123 (See formula 6) contains two parts of the piperidine structure (See formula 1). It is therefore expected that the effect of the compound of formula-1 (from TINUVIN-123) is twice that of the other compounds. TINUVIN-123 was therefore tested at half the amount of the other base quenchers (the quencher loading of TINUVAN-1123 was adjusted to have a quencher/PAG molar ratio of 0.069.

Preparation of Sample #1

90 grams (g) of Polymer-A (a copolymer of p-hydroxy styrene (PHS)/tert-butyl acrylate (TBA) of 64/36 molar ratio, weight average molecular weight Mw=23,000 g/mole obtained from Maruzen Petrochemical Co., LTD.) and 10 g of Polymer-B (a copolymer of PHS/styrene (STY)/TBA in a 66/19/15 molar ratio, (weight average molecular weight Mw=11,000 g/mole obtained from DuPont Electronic Polymer) was taken in a 500 milliliters (ml) plastic bottle. Against 100 parts of polymer, 1 part (1 g) of NHNI-PFBS (obtained from Toyo Gosei Co. LTD, Mw=495.27), 0.048 part (0.048 g) of 4H-TEMPO (weight average molecular weight Mw: 172.25 g/mole) and 1 part (1 g) of PIONIN ME-400 obtained from Takemoto Oil and Fat.) were added. Against a total of 102.048 g of material, 117 g of solvent mixture that consist of 95% of PMGEA (111.2 g) and 5% of GBL (5.8 g) were added to adjust the solids content to 46.5 wt %.

The ingredients used to manufacture Sample #1 were mixed on a roller shaker. The quencher (4H-TEMPO) and PAG (NHNI-PFBS) molar ratio is calculated as follows:

$$(0.0489 \text{ g}/172.25)/(1 \text{ g}/495.27)=0.139$$

Preparation of Samples #2 to #5

Samples #2 to #5 were prepared the same manner as Sample #1 and uses the same quencher/photoacid generator molar ratio. The only difference is the type of quencher used (as may be seen in Table 2 below). The quencher loading was adjusted to have the same quencher/PAG molar ratio (0.139) as that shown in the Example 2.

Sample #6

Sample #6 was prepared in the same manner as Sample #1 except for the type of quencher and the quencher/PAG molar ratio. The quencher was TINUVIN-123. For this sample, the quencher loading was adjusted to have a quencher/PAG molar ratio of 0.069.

TABLE 2

| | | Sample | | | | | |
|---|---|---|---|---|---|---|---|
| | | #1 | #2 | #3 | #4 | #5 | #6 |
| Polymer | Polymer-A, Mw = 22,530 PHS/STY/TBA = 64%/0/36 mol % | 90 | 90 | 90 | 90 | 90 | 90 |
| | Polymer-B, Mw = 10,716 PHS/STY/TBA = 66/19/15 mol % | 10 | 10 | 10 | 10 | 10 | 10 |
| PAG | N-nonafluorobutanesulfonyloxy-1,8-naphthalimide (NHNI-PFBS) | 1.00 | 1.00 | 1.00 | 1.00 | 1.00 | 1.00 |
| Quencher | Quencher loading wt % | 0.048 | 0.048 | 0.078 | 0.060 | 0.053 | 0.104 |
| | Quencher/PAG molar ratio | 0.139 | 0.139 | 0.139 | 0.139 | 0.139 | 0.069 |
| | Quencher | 4H-TEMPO | 4H-TEMP | 4-Benzoate-TEMPO | 4-Acetamide-TEMPO | 4-Methoxy-TEMPO | TINUVIN-123 |
| Additive | Plasticizer (PIONIN ME-400) (poly(oxy-1,2-ethanediyl), α-methyl-ω-hydroxy-polymer (a.k.a: PEG) | 1.0 | 1.0 | 1.0 | 1.0 | 1.0 | 1.0 |
| Solvent | PEGMEA | 95 | 95 | 95 | 95 | 95 | 95 |
| | GBL | 5 | 5 | 5 | 5 | 5 | 5 |
| | Solid %= | 46.5% | 46.5% | 46.5% | 46.5% | 46.5% | 46.5% |

All weights in Table 2 are in parts per hundred based on 100 parts of the Polymer A and Polymer B, except for the solids content, which is expressed in weight percent.

From the data obtained, it was seen that Sample #2 and #4 produced an overhung profile. An overhung profile is one where the sidewall angle is larger than 90° (degrees). In other words, when the width is compared at the surface and bottom of the photoresist pattern using a scanning electron microscopy cross-sectional image, the width at the surface is narrower than that at the bottom.

Other samples gave favorable entrance profiles. Thermal weight loss of 4H-TEMPO was better than 4H-TEMP and 4-methoxy-TEMPO. TINUVIN-123 also indicated no weight loss at up to 190° C., but Sample #6 indicated an angled sidewall. From these test results, it can be concluded that the favorable pattern profile is not dependent on the volatility of base quencher. For example, a quencher that has piperidine 1-oxyl structure gave a favorable profile regardless of substitution of the 4 position, except for the 4-acetamide-TEMPO. FIG. 7 shows a comparison of HALS analogues on a pattern profile of 25 μm (micrometers) for a 1:1 contact hole.

Without being limited to theory, it is believed that the overhung profile is produced because during the initial step, the fluorinated naphtalimide photoacid generator is cleaved by incident UV light. Then the chromophore part of intermediate, Chromophore Intermediate-1 forms Chromophore Intermediate-2 by a ring-opening reaction as shown in the FIG. 2.

The I-line exposure process and post exposure bake (PEB) process is conducted in an ambient atmosphere. This results in the presence of oxygen at the surface of the photoresist. Oxygen penetrates into the photoresist at the exposed surface. The highest oxygen concentration therefore exists at the surface of the photoresist. The depth of the penetration of oxygen into the photoresist depends on its polymer matrix composition, the solvent system used and/or the process conditions used.

Figure 2:
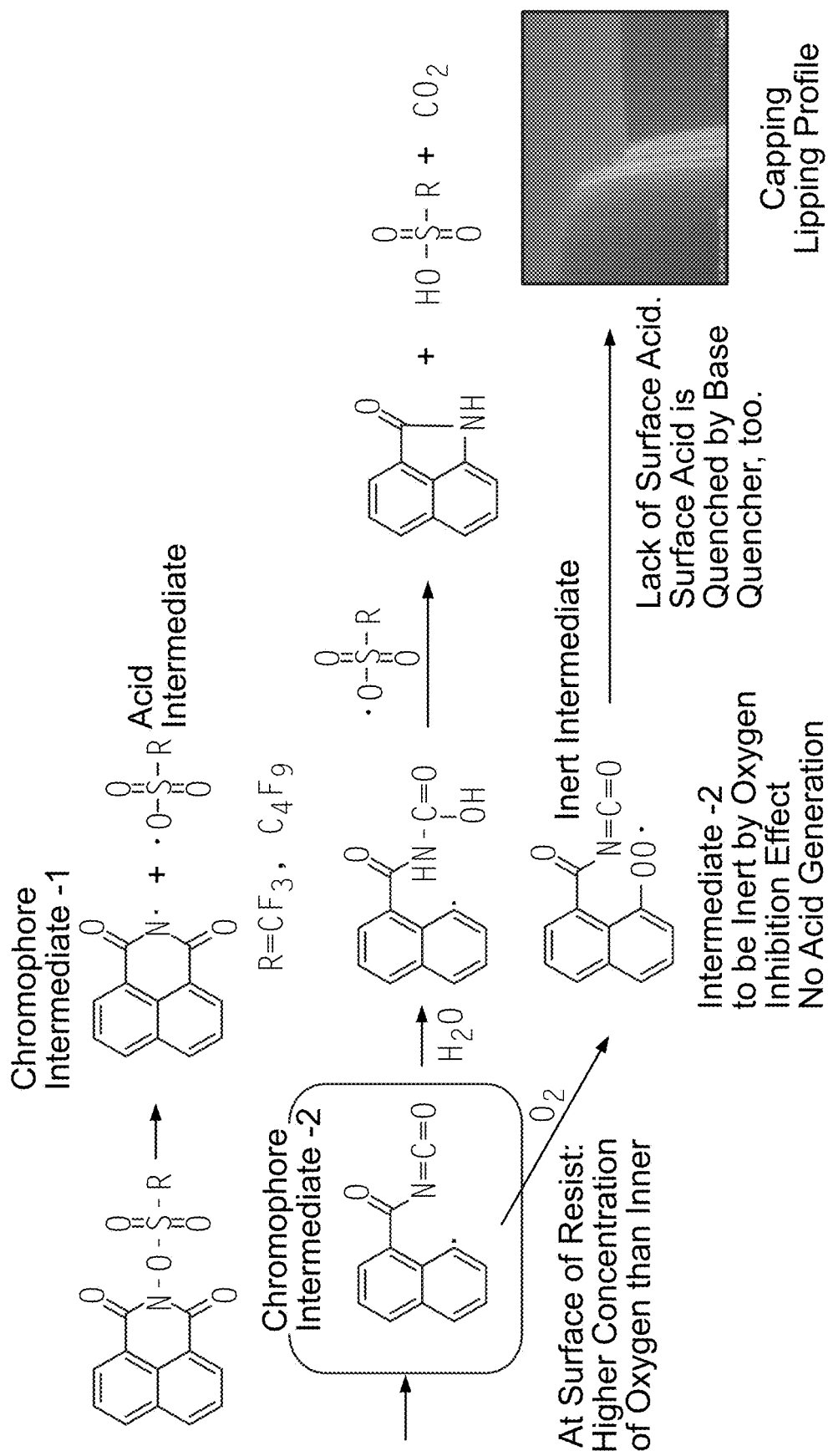
FIG. 2 depicts a reaction scheme for the proposed mechanism of the overhung profile by adopting Norish-1 cleavage model of acid generation for fluorinated naphtalimide photoacid generators.

At the surface, the Chromophore Intermediate-2 is scavenged by oxygen. The effect is known as the Oxygen Inhibition Effect. After the Intermediate-2 is scavenged, hydrolysis may not proceed. Thus the acid intermediate, the perfluoroalkylsulfonyl radical, does not abstract hydrogen from the hydrolyzed radical. As a result, the concentration of photo acid at the surface is lower than at the middle or bottom of the photoresist. This leads to a cross-sectional width (diameter) that is narrower at the surface than that at the bottom. This mechanism is shown in the FIG. 2. FIG. 2 depicts a reaction scheme for the proposed mechanism of the overhung profile by adopting Norish-1 cleavage model of acid generation for fluorinated naphtalimide photoacid generators.

When a TEMPO free radical is used in a photoresist, the Chromophore Intermediate-2 is scavenged by the TEMPO free radical to form a nitroxyl alkyl intermediate (NOR-TEMPO). As discussed above, the Chromophore Intermediate-2 is also scavenged by oxygen. The NOR-TEMPO and the oxidized intermediate regenerates the TEMPO free radical along with a proton. In this model, the generated proton is coupled with the acid part of intermediate to then generate a photo acid. It is believed that this reaction occurs where the oxygen concentration is high. Thus, TEMPO free radical or TINUVIN-123 (NOR-TEMPO) indicated favorable profile.

Figure 3:
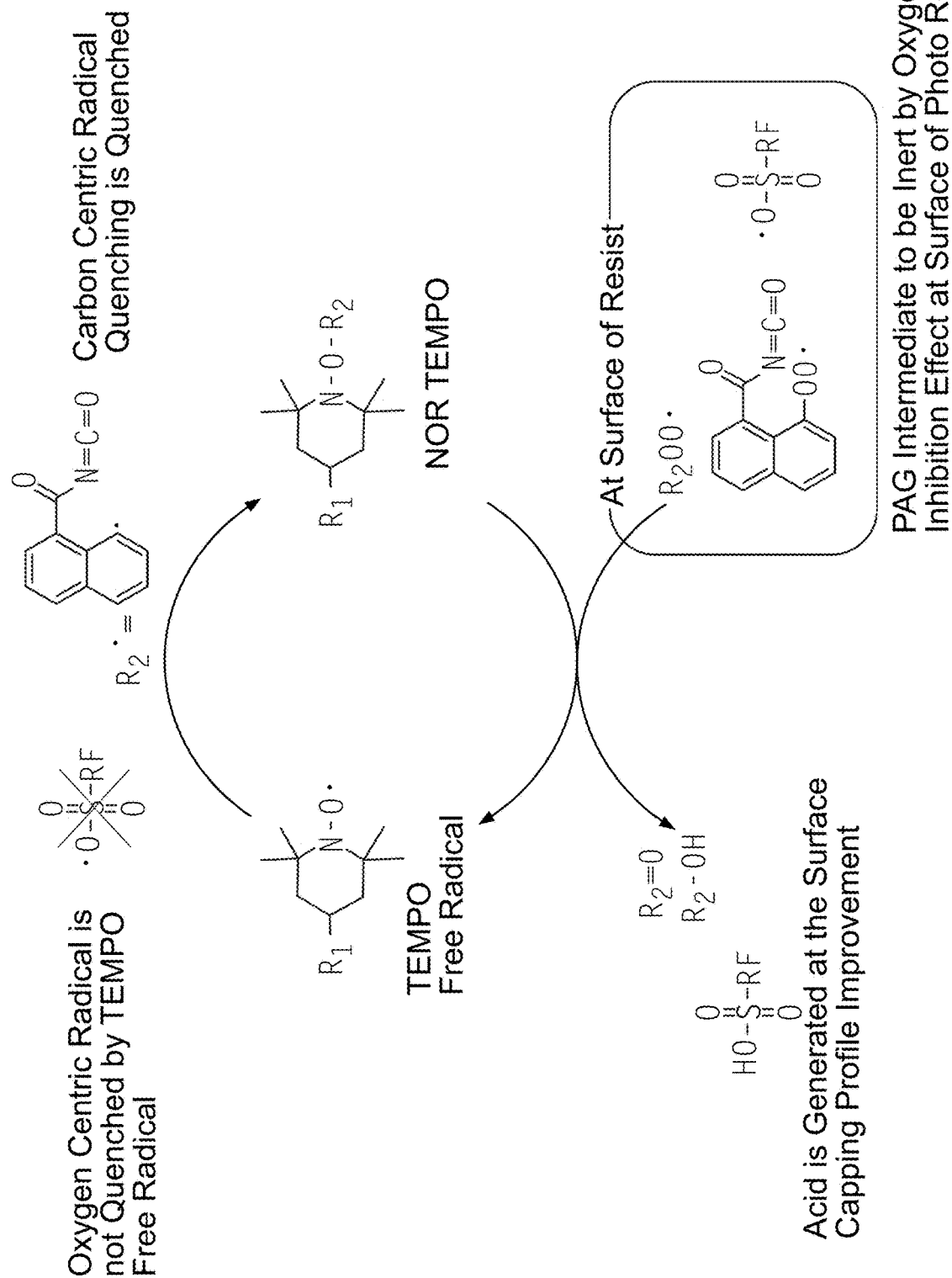
FIG. 3 depicts a reaction scheme for the proposed mechanism for a top rounding profile using TEMPO as scavenger.

In this proposed mechanism, the nitroxy structure of TEMPO plays a significant role. Thus, the 4H-TEMP (4-hydroxy-1,2,2,6,6-pentamethylpiperidine) indicates an overhung profile. However, 4-acetoamide-TEMPO (4-acetamido-2,2,6,6-tetramethylpiperidine 1-oxyl free radical), that has the nitroxyl structure, improves the overhung profile. FIG. 3 depicts a reaction scheme for the proposed mechanism for a top rounding profile using TEMPO as scavenger.

Example 3

This example was conducted to determine the effect of HALS compounds on PEB sensitivity and PED (Post Exposure Delay) stability. TINUVIN-123 was selected as an example of NOR-TEMPO type HALS. A combination of Troger's Base and benzotriazole was used as a base reference for the quencher. The effect of the plasticizer was also studied and compared against samples with different plasticizers or against samples with no plasticizers. LUTONAL M40 (weight average molecular weight $M_w=70,000$) was selected as the polymeric plasticizer. PIONIN M400 was used as a reference that has a lower weight average molecular weight ($M_w=400$).

Evaluations were conducted on 15 micron film thickness samples. (SB=135° C./60 sec, FT=15 PEB=90,100 and 110° C./60 sec, development time=60 sec puddle). A 15 micrometer (μm) isolated trench pattern was used for lithographic comparison. The photoresist was exposed by a broad band exposure tool (MA-1200). CD-exposure curve was taken on each condition. Sizing energy ($E_{op}$) of each sample, condition was determined from a CD-Exposure curve. The pattern size (CD) shift after 24 hour of PED at $E_{op}$ was then calculated. Table 4 shows formulation and lithographic test results.

TABLE 4

| | | | Samples | | | |
|---|---|---|---|---|---|---|
| | | | #7 | #8 | #9 | #10 |
| Actual loading | Polymer | Polymer-A | 100 | 100 | 100 | 100 |
| | PAG | NHNI-TF | 0.21 | 0.21 | 0.21 | 0.21 |
| | | NHNI-PFBS | 0.79 | 0.79 | 0.79 | 0.79 |
| | Base | Troger's Base | 0.047 | 0.046 | | |
| | | TINUVIN-123 | | | 0.182 | 0.182 |
| | | Benzotriazole | 0.022 | 0.022 | | |
| | Plasticizer | LUTONAL M40 | 3.9 | | 4.0 | |
| | | PIONINE M400 | | 1.0 | | 1.0 |
| | | BASE/PAG mol ratio | 0.166 | 0.166 | 0.112 | 0.112 |
| Test result | PEB 90° C. | $E_{th}$/mJ/cm$^2$ | 80 | 83 | 110 | 117 |
| | | $E_{op}$/mJ/cm$^2$ | 160 | 177 | 174 | 175 |
| | | CD Shift after 24 h PED/μm | −1.93 | −2.85 | −3.38 | — |
| | PEB 100° C. | $E_{th}$/mJ/cm$^2$ | 60 | 60 | 87 | 90 |
| | | $E_{op}$/mJ/cm$^2$ | 130 | 136 | 162 | 168 |
| | | CD Shift after 24 h PED/μm | −1.22 | −1.66 | −1.10 | −3.87 |
| | PEB 110° C. | $E_{th}$/mJ/cm$^2$ | 50 | 87 | 77 | 80 |
| | | $E_{op}$/mJ/cm$^2$ | 114 | 123 | 162 | 167 |
| | | CD Shift after 24 h PED/μm | −2.13 | −2.94 | −0.98 | −3.70 |
| | | PEB sensitivity/μm/° C. | 0.078 | 0.117 | 0.021 | 0.019 |

All weights in Table 4 are in parts per hundred based on 100 parts of the Polymer A.

In Table 4, CD stands for critical dimension and is measured via pattern size. $E_{th}$ stands for the minimum exposure energy to break through the film during specified development conditions. $E_{op}$ stands for the optimum exposure energy to give a desired pattern size-15 μm of pattern size was targeted for this experiment.

Figure 4:
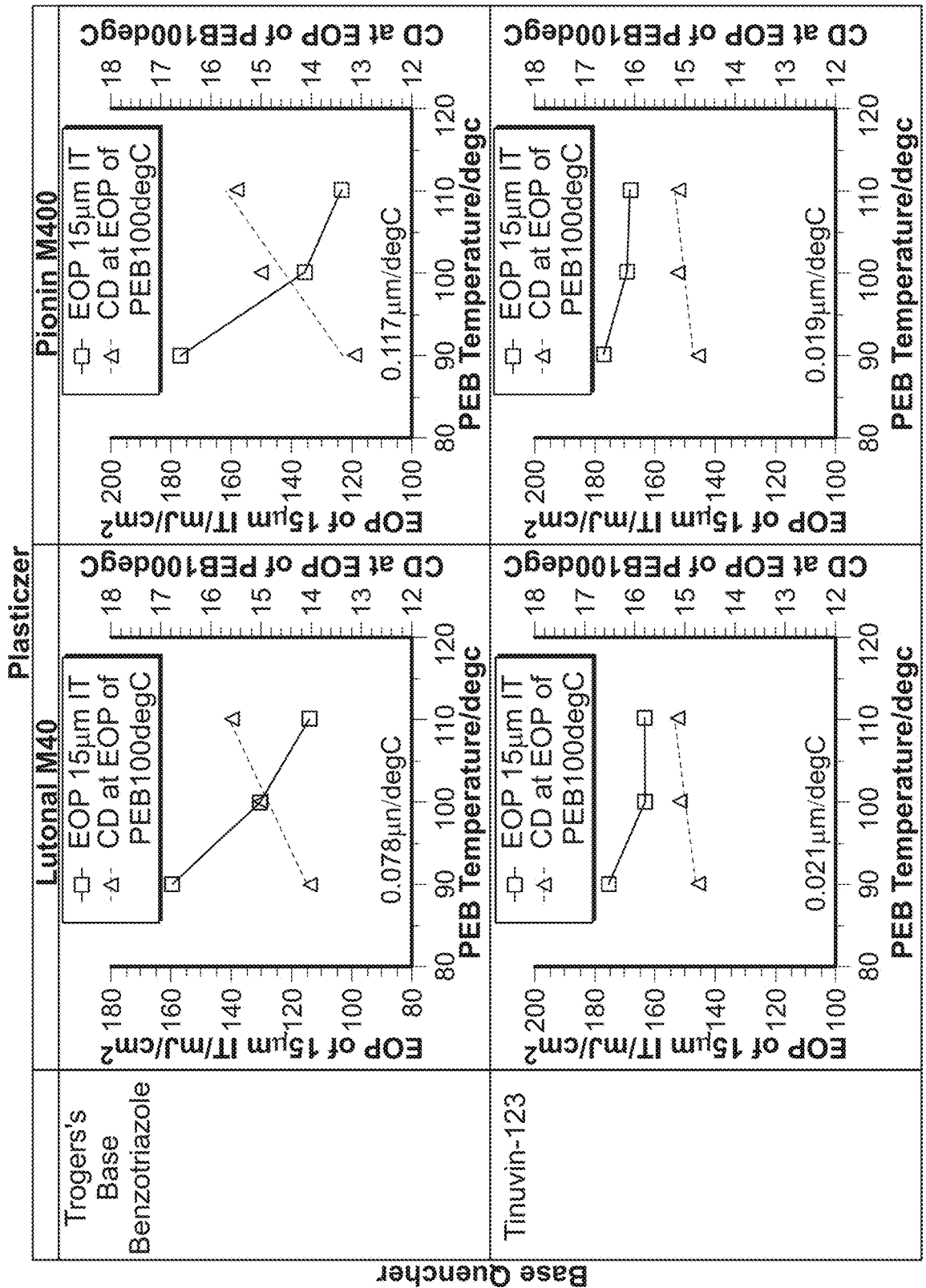
FIG. 4 depicts $E_{op}$ and CD shift against PEB temperature variation.

From the results in the Table 4, it may be seen that TINUVIN-123 imparts stability sensitivity (CD and $E_{op}$) against PEB temperature variations. LUTONAL M40 provides PED CD Stability as seen in the FIG. 4. FIG. 4 depicts $E_{op}$ and CD shift against PEB temperature variation.

Figure 5:
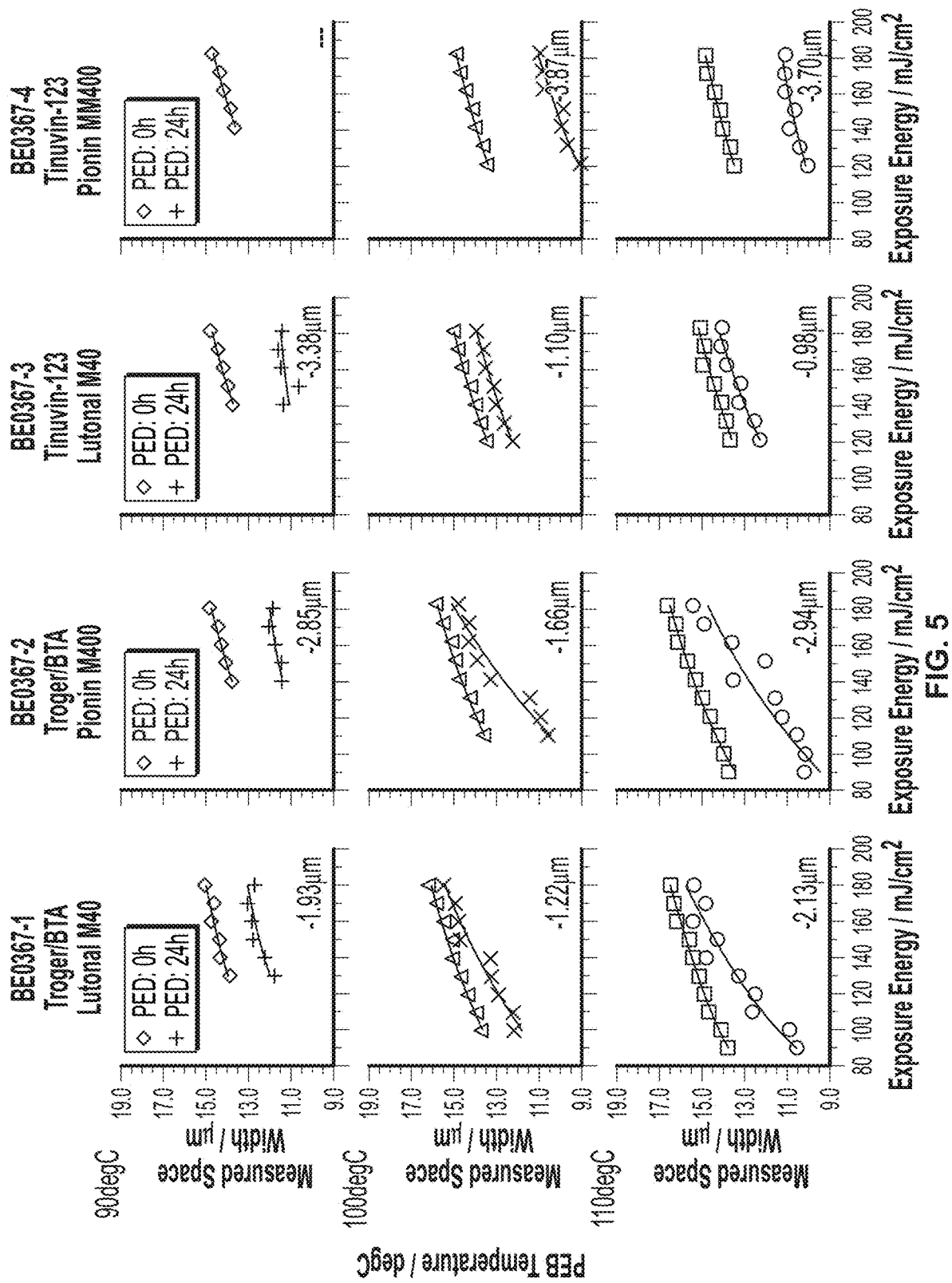
FIG. 5 shows that a polymeric plasticizer produced better PED stability when the PEB temperature is increased.

PED CD-shift was evaluated by split PEB temperature. LUTONAL M40 gave better PED stability. TINUVIN M40 gives better PED stability when the PEB temperature is increased as seen in the FIG. 5.

Comparing the cross section pattern profile shows that a combination of LUTONAL M40 and TINUVIN-123 give favorable pattern profiles before and after PED as seen in FIG. 6.

The radiation-sensitive compositions disclosed herein are advantageous in patterning and metallization processes. More specifically, the processes and compositions are useful in depositing a metal on a substrate, for example, for forming micro metal bumps on a metal layer. The invention finds particular use in the semiconductor manufacturing industry, for example, in semiconductor device and MEMS manufacturing, and in packaging applications such as in the formation of metal bumps for use in package on package, chip on chip or flip chip bonding of microprocessor or memory devices.

What is claimed is:

1. A radiation-sensitive composition comprising:
a photoacid generator;
a quencher that has the structure of formula (1)

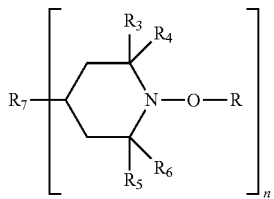

(1)

wherein $R_3$ to $R_6$ can be the same or different and are substituted or unsubstituted alkyls having 1 to 10 carbon atoms and wherein R is a radical or a substituted or unsubstituted alkyl having 1 to 10 carbon atoms, wherein $R_7$ is a group having the structure of formula (2):

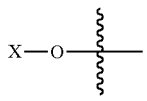

(2)

where X is a hydrogen atom or comprises carbonyl group, an ester group, a carbonate group, an amine group, an amide group, a urea group, a sulfate group, a sulfone group, a sulfoxide group, an N-oxide group, a sulfonate group, a sulfonamide group, or a combination thereof, a substituted or unsubstituted $C_6$ to $C_{14}$ aryl group, or $C_3$ to $C_{12}$ heteroaryl group, wherein the substitution is halogen, hydroxyl, cyano, nitro, $C_1$ to $C_{12}$ alkyl group, $C_1$ to $C_{12}$ haloalkyl group, $C_1$ to $C_{12}$ alkoxy group, $C_3$ to $C_{12}$ cycloalkyl group, amino, $C_2$-$C_6$ alkanoyl, carboxamido, a substituted or unsubstituted $C_6$ to $C_{14}$ aryl group, or $C_3$ to $C_{12}$ heteroaryl group; wherein n is 1 or 2;
an acid labile polymer formed from monomers comprising a vinyl aromatic monomer and a monomer comprising an acid decomposable group; wherein the acid decomposable group is a tertiary alkyl ester group; and
a solvent.

2. The radiation-sensitive composition of claim 1, where the photoacid generator has a structure of formula (7)

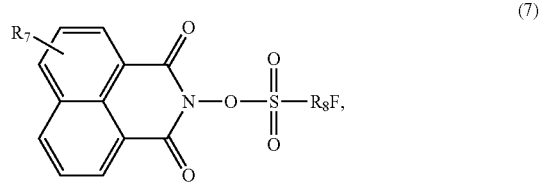

(7)

wherein $R_7$ is a hydrogen atom, a substituted or unsubstituted linear or branched $C_1$ to $C_{14}$ alkyl group, a substituted heterocyclic group, or a halogen atom; and wherein $R_8$ is a substituted or unsubstituted alkyl group having 1 to 18 carbon atoms, a halogen atom, or an aryl group having 6 to 20 unsubstituted carbon atoms.

3. The radiation-sensitive composition of claim 1, further comprising a polymeric adhesion promotor, where the polymeric adhesion promotor is the polymerization compound of the structure of formula (13)

(13)

wherein $R_{21}$ is a substituted or unsubstituted alkyl group having 1 to 18 carbon atoms.

4. The radiation-sensitive composition of claim 1, wherein the vinyl aromatic monomoer is hydroxystyrene and wherein the monomer comprising the acid decomposable group is a (meth)acrylic monomer that comprises a tertiary carbon as an acid labile species and wherein the acid labile polymer has a weight average molecular weight of 10,000 to 30,000 grams per mole.

5. The radiation-sensitive composition of claim 1, further comprising an aromatic azole compound; wherein the aromatic azole compound is a benzotriazole derivative having the structure of formula (14):

(14)

wherein $R_{22}$ is an alkyl group having 1 to 14 carbon atoms or an amine group.

6. The radiation-sensitive composition of claim 1, wherein the photoacid generator is present in an amount of less than 2 wt % of a total amount of the monomer that comprises the acid decomposable group.

7. The radiation-sensitive composition of claim 1, wherein the acid labile polymer further comprises a second vinyl aromatic monomer.

8. The radiation-sensitive composition of claim 1, wherein the quencher is a base quencher, wherein an amount of the base quencher is present in an amount of 0.1 to 50 mole percent based on a total number of moles of the photoacid generator.

9. A method of forming a resist pattern comprising:
forming a radiation-sensitive film on a substrate; wherein the radiation-sensitive film comprises the radiation-sensitive composition of claim 1;
patternwise exposing the radiation-sensitive film to activating radiation; and
contacting the radiation-sensitive film with an alkaline developing solution to form a resist pattern.

\* \* \* \* \*